(12) United States Patent
Guo et al.

(10) Patent No.: US 11,787,814 B2
(45) Date of Patent: Oct. 17, 2023

(54) METHOD FOR PREPARING 2-INDOLINOSPIRONE COMPOUND AND INTERMEDIATE THEREOF

(71) Applicants: Ascentage Pharma (Suzhou) Co., Ltd., Jiangsu (CN); Ascentage Pharma Group Corp Limited, Hong Kong (CN)

(72) Inventors: Ming Guo, Suzhou (CN); Jianfeng Wen, Suzhou (CN); Jianpeng Feng, Suzhou (CN); Tianzhu Wu, Suzhou (CN); Huirong Lu, Suzhou (CN)

(73) Assignees: Ascentage Pharma (Suzhou) Co., Ltd., Jiangsu (CN); Ascentage Pharma Group Corp Limited, Hong Kong (CN)

( * ) Notice: Subject to any disclaimer, the term of this patent is extended or adjusted under 35 U.S.C. 154(b) by 142 days.

(21) Appl. No.: 17/265,459

(22) PCT Filed: Jul. 10, 2020

(86) PCT No.: PCT/CN2020/101226
§ 371 (c)(1),
(2) Date: Feb. 2, 2021

(87) PCT Pub. No.: WO2021/004516
PCT Pub. Date: Jan. 14, 2021

(65) Prior Publication Data
US 2021/0261558 A1    Aug. 26, 2021

(30) Foreign Application Priority Data
Jul. 11, 2019  (WO) ............... PCT/CN2019/095604
Jun. 30, 2020  (CN) .......................... 202010617212.X

(51) Int. Cl.
*C07D 487/10* (2006.01)
(52) U.S. Cl.
CPC ................... *C07D 487/10* (2013.01)
(58) Field of Classification Search
CPC .................................................. C07D 487/10
See application file for complete search history.

(56) References Cited

U.S. PATENT DOCUMENTS

| 9,745,314 | B2 | 8/2017 | Wang et al. |
| 10,030,028 | B2 | 7/2018 | Yamauchi et al. |

FOREIGN PATENT DOCUMENTS

| CN | 105555789 A | 5/2016 |
| CN | 106794171 A | 5/2017 |

OTHER PUBLICATIONS

Aguilar et al., "Discovery of 4-((3'R,4'S,5'R)-6"-Chloro-4'-(3-chloro-2-fluorophenyl)-1'-ethyl-2"-oxodispiro[cyclohexane-1,2'-pyrrolidine-3',3"-indoline]-5'-carboxamido)bicyclo[2.2.2]octane-1-carboxylic Acid (AA-115/APG-115): A Potent and Orally Active Murine Double Minute 2 (MDM2) Inhibitor in Clinical Development," *J. Med. Chem.*, 60(7):2819-2839 (2017).

*Primary Examiner* — Rebecca L Anderson
(74) *Attorney, Agent, or Firm* — Jones Day

(57) ABSTRACT

Disclosed is a method for preparing 2-indolinospirone compound and intermediate thereof, specifically disclosed is a method for preparing a compound of formula 5. The method is relatively simple and has high stereoselectivity and yield.

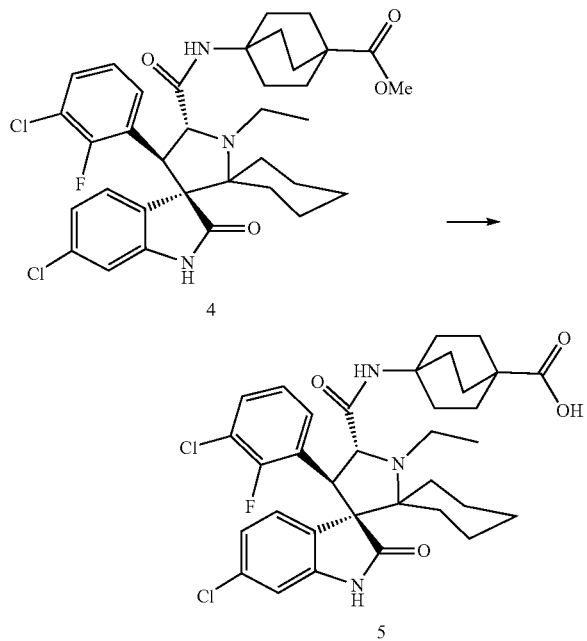

16 Claims, No Drawings

METHOD FOR PREPARING 2-INDOLINOSPIRONE COMPOUND AND INTERMEDIATE THEREOF

This application is a national phase entry pursuant to 35 U.S.C. § 371 of International Application No. PCT/CN2020/101226, filed on Jul. 10, 2020, which claims the benefits of international patent application No. PCT/CN2019/095604, filed on Jul. 11, 2019 and Chinese patent application No. CN202010617212.X, filed on Jun. 30, 2020, the contents of all of which are incorporated herein by reference in their entireties.

TECHNICAL FIELD

The present disclosure relates to a method for preparing 2-indolinospirone compound and intermediate thereof.

BACKGROUND ART

The p53 tumor suppressor plays a central role in controlling cell cycle progression, senescence and apoptosis. MDM2 and p53 are part of an auto-regulatory feed-back loop. MDM2 is transcriptionally activated by p53 and MDM2. The prior art has disclosed that a class of 2-indolinospirone compounds, which have inhibitory activities of MDM2 and MDM2-related proteins and can effectively treat, improve or prevent hyperproliferative diseases. Hyperproliferative diseases can be a variety of solid tumor diseases that are common in humans, such as bile duct cancer, bladder cancer, bone cancer, breast cancer, Castleman disease, cervical cancer, colon/rectum cancer, endometrial cancer, esophagus cancer and the like. One of the 2-indolinospirone compounds is shown below:

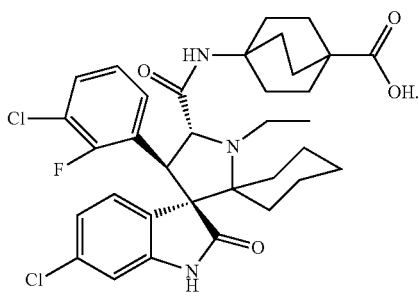 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

Content of the Disclosure

The technical problem to be solved by the present disclosure is to provide a novel method for preparing 2-indolinospirone compound and intermediate thereof. The preparation method is simple and has high stereoselectivity and yield.

The present disclosure provides a compound of formula 2:

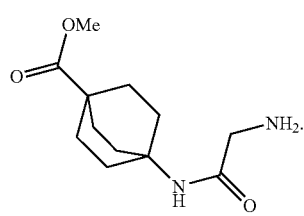

The present disclosure further provides a method for preparing a compound of formula 3, which comprises carrying out a 1,3-dipolar cycloaddition reaction of compound of formula 1, compound of formula 2 and cyclohexanone in an organic solvent in the presence of a metal source, a phosphine ligand and a base to obtain the compound of formula 3;

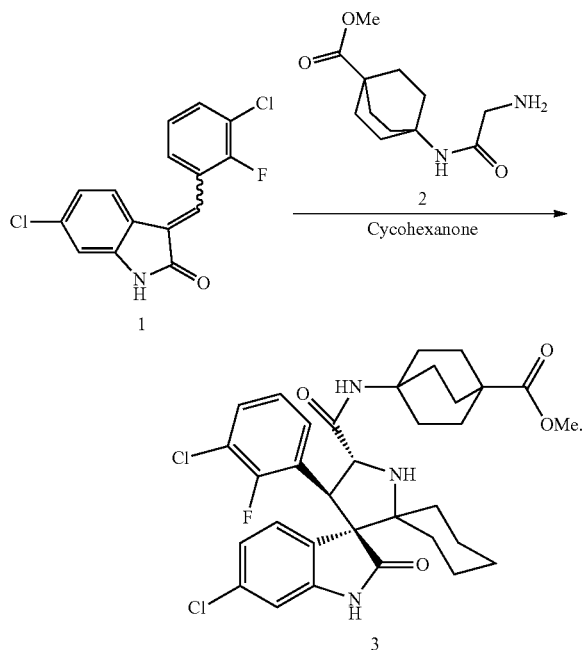

The 1,3-dipolar cycloaddition reaction can be carried out under a protective gas atmosphere (e.g, one or more selected from the group consisting of nitrogen, helium, neon, argon, krypton, and xenon).

In the 1,3-dipolar cycloaddition reaction, the organic solvent can be a conventional solvent used in this type of reaction in the art, such as one or more selected from the group consisting of an aromatic solvent (e.g., toluene and/or xylene, e.g, toluene), an ester solvent (e.g., ethyl acetate and/or isopropyl acetate), a cycloalkane solvent (e.g, one or more selected from the group consisting of cyclopentane, cyclohexane, and cycloheptane, e.g, cyclohexane), an ether solvent (e.g., diethyl ether and/or tetrahydrofuran), a halogenated alkane solvent (e.g, chloroalkane solvent, such as one or more selected from the group consisting of chloroform, dichloromethane, and 1,2-dichloroethane), a nitrile solvent (e.g, acetonitrile), and an amide solvent (e.g., N,N-dimethylacetamide and/or N,N-dimethylformamide). In some embodiments, the organic solvent is a cycloalkane solvent and/or an aromatic solvent. In some embodiments, the organic solvent is a cycloalkane solvent. In some embodiments, the organic solvent is cyclohexane. In some embodiments, the organic solvent is toluene.

In the 1,3-dipolar cycloaddition reaction, the amount of the organic solvent can be adjusted according to the reaction scale, the solubility of the raw materials, and the like, for example, the volume/mass ratio of the organic solvent to the compound of formula 1 can be 10:1 to 50:1 mL/g (e.g., 20:1 to 40:1 mL/g).

In the 1,3-dipolar cycloaddition reaction, the molar ratio of the compound of formula 2 to the compound of formula 1 can be 1:1 to 5:1, e.g, 1:1 to 3:1, e.g, 1:1, 1.2:1, 1.5:1, 2:1 or 2.7:1, e.g, 1.5:1 to 2.7:1.

In the 1,3-dipolar cycloaddition reaction, the molar ratio of the cyclohexanone to the compound of formula 1 can be 1:1 to 10:1, e.g., 1:1 to 8:1, e.g., 1:1, 2:1, 3:1, 4:1, 5:1, 6:1, 7:1 or 8:1.

In the 1,3-dipolar cycloaddition reaction, the base can be an organic base and/or an inorganic base. The organic base can be one or more selected from the group consisting of pyridine, piperidine, DBU (1,8-diazabicyclo[5.4.0]undec-7-ene), DABCO (1,4-diazabicyclo [2.2.2] octane), and

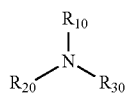

(e.g., triethylamine and/or diisopropylethylamine); wherein each of $R_{10}$, $R_{20}$ and $R_{30}$ is independently hydrogen or $C_1$-$C_4$ alkyl. The inorganic base can be one or more selected from the group consisting of an alkali metal alkoxide (e.g., potassium tert-butoxide and/or sodium tert-butoxide), an alkali metal carbonate (e.g, potassium carbonate and/or sodium carbonate) and an alkali metal hydroxide (e.g, sodium hydroxide and/or potassium hydroxide). In some embodiments, the base is an organic base. In some embodiments, the base is

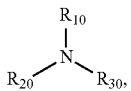

wherein each of $R_{10}$, $R_{20}$ and $R_{30}$ is independently hydrogen or $C_1$-$C_4$ alkyl. In some embodiments, the base is triethylamine and/or diisopropylethylamine. In some embodiments, the base is triethylamine.

In the 1,3-dipolar cycloaddition reaction, the molar ratio of the base to the compound of formula 1 can be 0.01:1 to 2.5:1, e.g., 0.1:1 to 2:1, e.g., 0.1:1 to 1.5:1, e.g., 0.1:1 to 0.3:1, e.g. 0.1:1, 0.2:1, 0.27:1, 0.3:1, 0.5:1, 1:1 or 1.5:1.

The reaction temperature of the 1,3-dipolar cycloaddition reaction can be 20° C. to the reflux temperature of the organic solvent, such as 50° C. to the reflux temperature of the organic solvent.

In the 1,3-dipolar cycloaddition reaction, the metal source can be one or more selected from the group consisting of Cu(I) source, Cu(II) source, Ag(I) source, Mg(II) source, Zn(II) source, Ni(II) source and Fe(II) source.

The Cu(I) source can be one or more selected from the group consisting of CuOAc, CuBr, $CU_2O$, CuCl, CuI and $CuPF_6$. In some embodiments, the Cu(I) source is CuOAc.

The Cu(II) source can be $Cu(OTf)_2$ and/or $Cu(OAc)_2$. In some embodiments, the Cu(II) source is $Cu(OAc)_2$.

The Ag(I) source can be one or more selected from the group consisting of AgOAc, AgF, AgBr, and AgOTf. In some embodiments, the Ag(I) source can be AgOAc.

The Mg(II) source can be MgCb and/or $MgBr_2$. In some embodiments, the Mg(II) source is $MgBr_2$.

The Zn(II) source can be $Zn(OTf)_2$ and/or $Zn(OAC)_2$.

The Ni(II) source can be $NiCl_2$ and/or $Ni(ClO_4)_2$.

The Fe(II) source can be $FeCl_2$ and/or $FeBr_2$. In some embodiments, the Fe(II) source is $FeCl_2$.

In some embodiments, the metal source is one or more selected from the group consisting of Cu(I) source, Cu(II) source, Ag(I) source, Mg(II) source and Fe(II) source.

In some embodiments, the metal source is one or more selected from the group consisting of Cu(I) source, Cu(II) source, and Fe(II) source.

In some embodiments, the metal source is Cu(I) source and/or Cu(II) source.

In some embodiments, the metal source is Cu(I) source and/or Cu(II) source, wherein the Cu(I) source is CuOAc, and the Cu(II) source is $Cu(OAc)_2$.

In some embodiments, the metal source is Cu(I) source, wherein the Cu(I) source is CuOAc.

In some embodiments, the metal source is Cu(II) source, wherein the Cu(II) source is $CU(OAC)_2$.

The molar ratio of the metal source to the compound of formula 1 can be 0.01:1 to 1:1, e.g., 0.05:1 to 0.5:1, e.g., 0.05:1, 0.1:1, 0.13:1, 0.2:1 or 0.3:1.

In the 1,3-dipolar cycloaddition reaction, the phosphine ligand can be a conventional phosphine ligand of this type of reaction in the art, such as one or more selected from the group consisting of a phosphine ligand of formula 6:

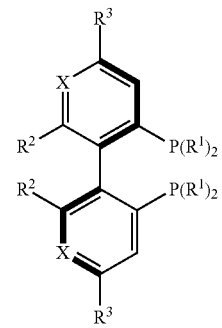

wherein $R^1$ is phenyl, which is optionally substituted by one, two or three substituents independently selected from the group consisting of $C_{1-4}$ alkyl and $C_{1-4}$ alkoxy;

$R^2$ is hydrogen, $C_{1-4}$ alkyl, or $C_{1-4}$ alkoxy; alternatively, two $R^2$ are connected to each other and together with the atoms to which they are attached form a 7- to 12-membered carbocyclic ring (e.g., 7-, 8-, 9-, 10-, 11 or 12-membered carbocyclic ring) or 7- to 12-membered heterocyclic ring (e.g., 7-, 8-, 9-, 10-, 11- or 12-membered heterocyclic ring), the 7- to 12-membered heterocyclic ring contains one, two or three oxygen atoms;

$R^3$ is hydrogen, $C_{1-4}$ alkyl or $C_{1-4}$ alkoxy;

X is N or $CR^4$;

$R^4$ is hydrogen, $C_{1-4}$ alkyl or $C_{1-4}$ alkoxy; alternatively, $R^4$, its adjacent $R^2$, and together with the atoms to which they are attached form a 5- to 7-membered carbocyclic ring (e.g, 5-, 6- or 7-membered carbocyclic ring) or a 5- to 7-membered heterocyclic ring (e.g., 5-, 6- or 7-membered heterocyclic ring), the 5- to 7-membered heterocyclic ring contains one, two or three oxygen atoms.

In some embodiments, the structure of the phosphine ligand of formula 6 is as follows:

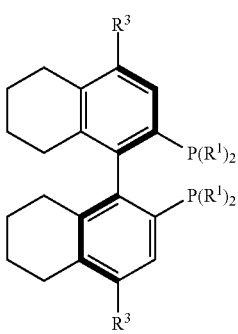

6-1 wherein $R^1$ and $R^3$ are as defined above.

When the phosphine ligand is a phosphine ligand of formula 6-1, the phosphine ligand of formula 6-1 can be

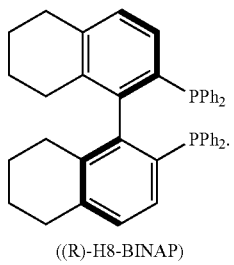

((R)-H8-BINAP)

In some embodiments, the structure of the phosphine ligand of formula 6 is as follows:

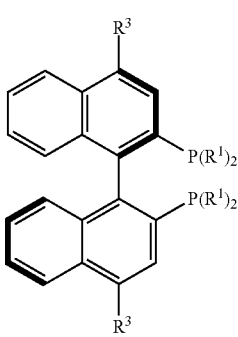

6-2 wherein $R^1$ and $R^3$ are as defined above.

When the phosphine ligand is a phosphine ligand of formula 6-2, the phosphine ligand of formula 6-2 can be

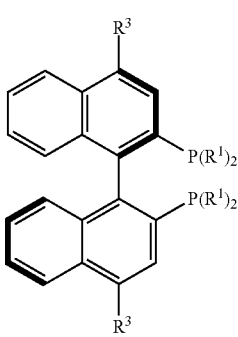

(R-BINAP)

In some embodiments, the structure of the phosphine ligand of formula 6 is as follows:

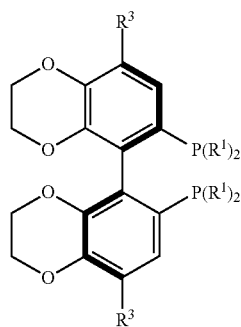

6-3 wherein $R^1$ and $R^3$ are as defined above.

When the phosphine ligand is a phosphine ligand of formula 6-3, the phosphine ligand of formula 6-3 can be

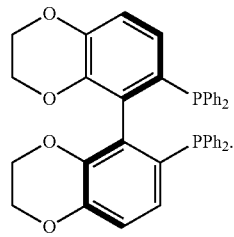

In some embodiments, the structure of the phosphine ligand of formula 6 is as follows:

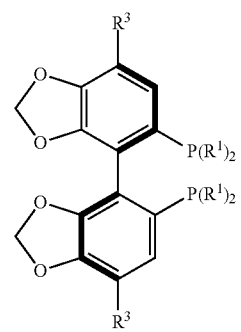

6-4 wherein $R^1$ and $R^3$ are as defined above.

When the phosphine ligand is a phosphine ligand of formula 6-4, the phosphine ligand of formula 6-4 can be

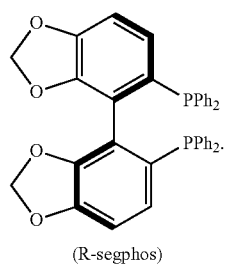

(R-segphos)

In some embodiments, the structure of the phosphine ligand of formula 6 is as follows:

6-5

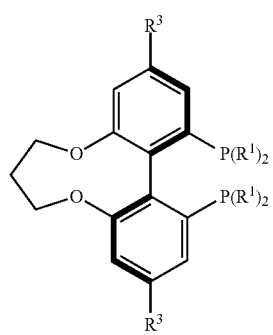

wherein $R^1$ and $R^3$ are as defined above.

When the phosphine ligand is a phosphine ligand of formula 6-5, the phosphine ligand of formula 6-5 can be

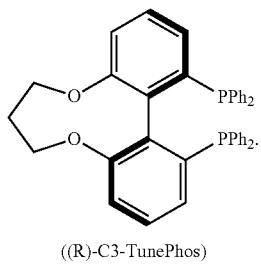

((R)-C3-TunePhos)

In some embodiments, the structure of the phosphine ligand of formula 6 is as follows:

6-6

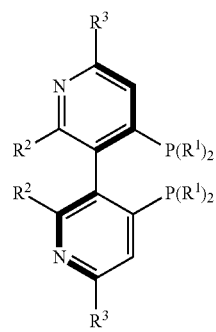

wherein $R^1$, $R^2$ and $R^3$ are as defined above.

When the phosphine ligand is a phosphine ligand of formula 6-6, the phosphine ligand of formula 6-6 can be

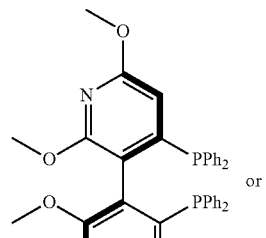

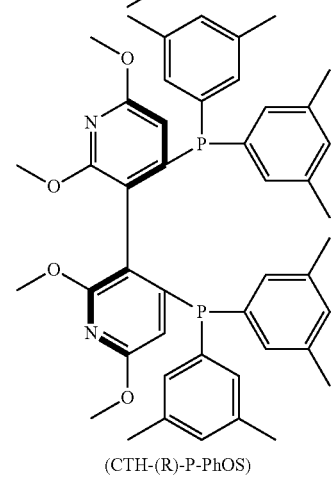

(CTH-(R)-P-PhOS)

In some embodiments, the structure of the phosphine ligand of formula 6 is as follows:

6-7

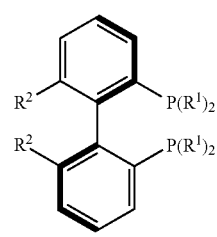

wherein $R^1$ and $R^2$ are as defined above.

When the phosphine ligand is a phosphine ligand of formula 6-7, the phosphine ligand of formula 6-7 can be

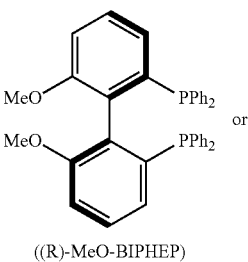

((R)-MeO-BIPHEP)

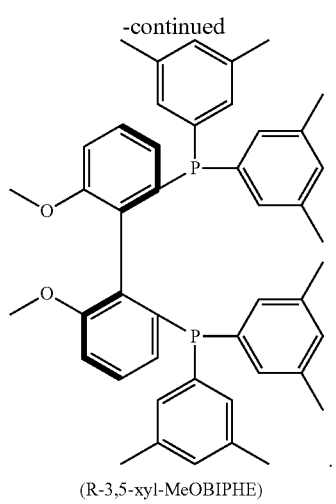

(R-3,5-xyl-MeOBIPHE)

In some embodiments, the phosphine ligand is the phosphine ligand of formula 6-1, the phosphine ligand of formula 6-2, the phosphine ligand of formula 6-4, the phosphine ligand of formula 6-5, the phosphine ligand of formula 6-6 or the phosphine ligand of formula 6-7.

In some embodiments, the phosphine ligand is the phosphine ligand of formula 6-2, the phosphine ligand of formula 6-4, the phosphine ligand of formula 6-5, the phosphine ligand of formula 6-6 or the phosphine ligand of formula 6-7.

In some embodiments, the phosphine ligand is

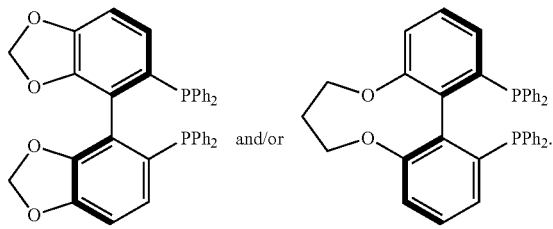

In some embodiments, the phosphine ligand is

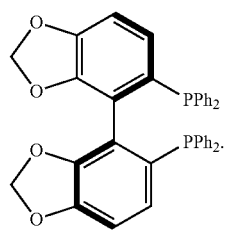

In some embodiments, the phosphine ligand is

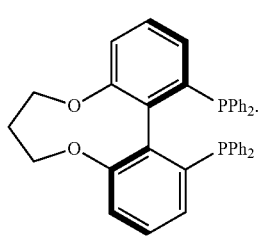

In the 1,3-dipolar cycloaddition reaction, the molar ratio of the phosphine ligand to the compound of formula 1 can be 0.01:1 to 1:1, e.g., 0.05:1 to 0.5:1, e.g., 0.05:1 to 0.3:1, e.g., 0.05:1, 0.06:1, 0.1:1, 0.13:1, 0.2:1, or 0.3:1.

In some embodiments, in the 1,3-dipolar cycloaddition reaction: the phosphine ligand is a phosphine ligand of formula 6 as described in any one of the above embodiments;

the metal source is Cu(I) source and/or Cu(II) source;

the organic solvent is a cycloalkane solvent and/or an aromatic solvent, such as a cycloalkane solvent, e.g, cyclohexane.

In some embodiments, in the 1,3-dipolar cycloaddition reaction:
the phosphine ligand is

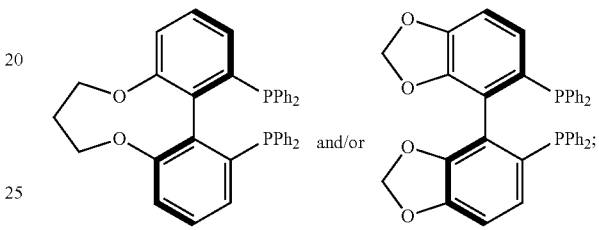

the metal source is Cu(I) source, wherein the Cu(I) source is CuOAc;

and the organic solvent is a cycloalkane solvent and/or an aromatic solvent, such as a cycloalkane solvent, e.g., cyclohexane.

In some embodiments, in the 1,3-dipolar cycloaddition reaction:
the phosphine ligand is

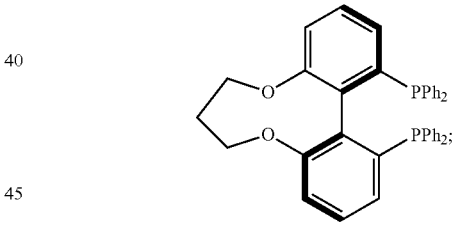

the metal source is Cu(I) source, wherein the Cu(I) source is CuOAc;
and the organic solvent is cyclohexane.

In some embodiments, in the 1,3-dipolar cycloaddition reaction:
the phosphine ligand is

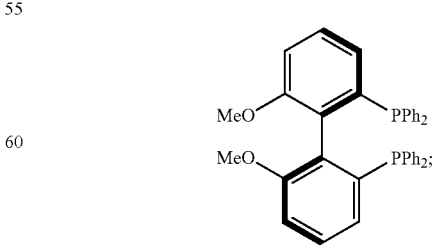

the metal source is Cu(I) source, wherein the Cu(I) source is CuOAc;

and the organic solvent is cyclohexane and/or toluene.

In some embodiments, in the 1,3-dipolar cycloaddition reaction:
the phosphine ligand is

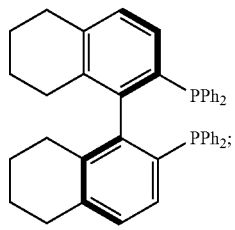

the metal source is Cu(I) source, wherein the Cu(I) source is CuOAc;
and the organic solvent is cyclohexane.

In some embodiments, in the 1,3-dipolar cycloaddition reaction:
the phosphine ligand is

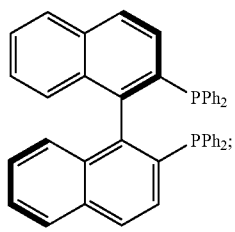

the metal source is Cu(I) source, wherein the Cu(I) source is CuOAc;
and the organic solvent is cyclohexane.

In some embodiments, in the 1,3-dipolar cycloaddition reaction:
the phosphine ligand is

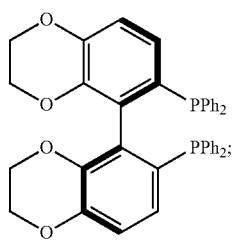

the metal source is Cu(I) source, wherein the Cu(I) source is CuOAc;
and the organic solvent is cyclohexane.

In some embodiments, in the 1,3-dipolar cycloaddition reaction:
the phosphine ligand is

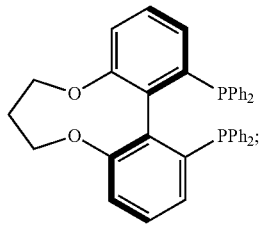

the metal source is Cu(I) source, wherein the Cu(I) source is CuOAc;
and the organic solvent is cyclohexane.

In some embodiments, in the 1,3-dipolar cycloaddition reaction:
the phosphine ligand is

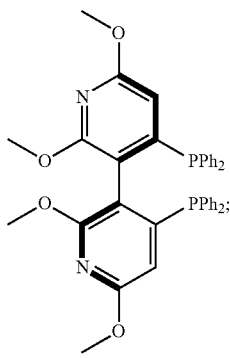

the metal source is Cu(I) source, wherein the Cu(I) source is CuOAc;
and the organic solvent is cyclohexane.

In some embodiments, in the 1,3-dipolar cycloaddition reaction:
the phosphine ligand is

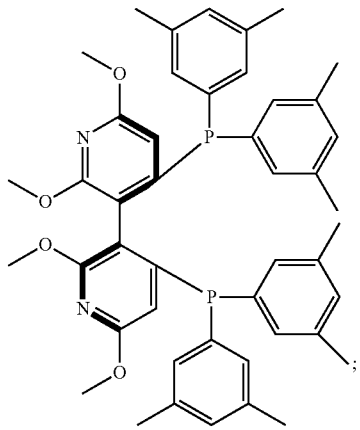

the metal source is Cu(I) source, wherein the Cu(I) source is CuOAc;
and the organic solvent is cyclohexane.

In some embodiments, in the 1,3-dipolar cycloaddition reaction:

the phosphine ligand is

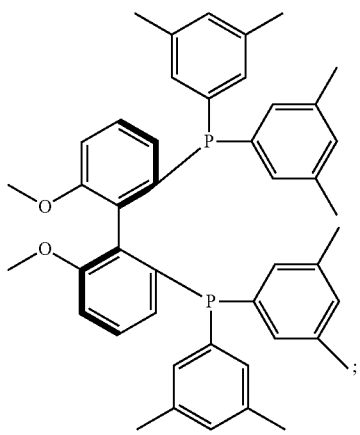

the metal source is Cu(I) source, wherein the Cu(I) source is CuOAc;
and the organic solvent is cyclohexane.

In some embodiments, in the 1,3-dipolar cycloaddition reaction:
the phosphine ligand is

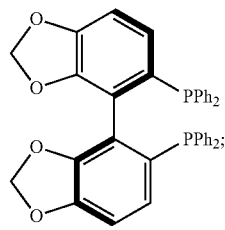

the metal source is Cu(I) source, wherein the Cu(I) source is CuOAc;
and the organic solvent is cyclohexane.

In some embodiments, in the 1,3-dipolar cycloaddition reaction: the phosphine ligand is

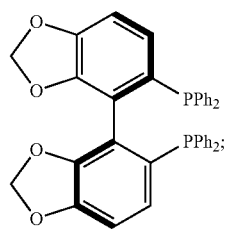

the metal source is Cu(II) source, wherein the Cu(II) source is Cu(OAc)$_2$;
and the organic solvent is cyclohexane.

The progress of the 1,3-dipolar cycloaddition reaction can be monitored by conventional testing methods in the art (e.g., TLC, HPLC, GC, or NMR), and a person skilled in the art can determine when to stop the reaction in order to obtain better reaction results according to the testing results (including the conversion degree of the raw materials, the formation of impurities, etc.). The reaction time of the 1,3-dipolar cycloaddition reaction can be 5-40 hours, such as 18-24 hours.

After the completion of the 1,3-dipolar cycloaddition reaction, the method can further comprise a post-treatment step, for example, filtering the reaction mixture and drying the resultant filter cake to obtain a crude compound of formula 3. The crude compound of formula 3 can be further purified by recrystallization. The solvent for the recrystallization (e.g., a method of dissolving by heating and crystallizing by cooling) can be one or more selected from the group consisting of an ester solvent (e.g, ethyl acetate), tetrahydrofuran, and an alcohol solvent (e.g, one or more selected from the group consisting of methanol, ethanol, and isopropanol). Multiple recrystallizations can be performed to obtain a product with higher purity.

In the method for preparing the compound of formula 3, the compound of formula 2 can be prepared by a method comprising carrying out a de-Boc reaction of a compound of formula C in a solvent in the presence of an acid;

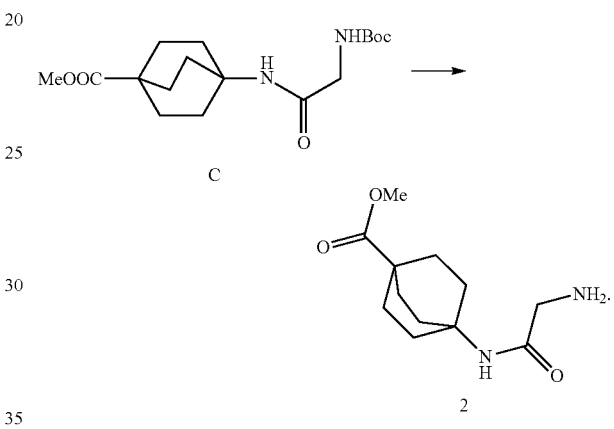

The conditions for the de-Boc reaction can be conventional conditions for this type of reaction in the art.

In the de-Boc reaction, the solvent can be a chloroalkane solvent (e.g, one or more selected from the group consisting of dichloromethane, chloroform, and 1,2-dichloroethane), an aromatic solvent (e.g, toluene and/or xylene), an alcohol solvent (e.g, methanol and/or ethanol), an ether solvent (e.g, diethyl ether and/or tetrahydrofuran), a nitrile solvent (e.g, acetonitrile), and an amide solvent (e.g, N,N-dimethylformamide). In some embodiments, the solvent is an alcohol solvent.

In the de-Boc reaction, the acid can be an inorganic acid (e.g., hydrogen chloride and/or sulfuric acid) and/or an organic acid (e.g., trifluoroacetic acid and/or p-toluenesulfonic acid). In one embodiment, the inorganic acid is hydrogen chloride.

In the de-Boc reaction, the molar ratio of the acid to the compound of formula C can be 1:1 to 20:1, e.g., 5:1 to 10:1.

In some embodiments, in the de-Boc reaction, the solvent is an alcohol solvent, and the acid is hydrogen chloride.

The progress of the de-Boc reaction can be monitored by conventional testing methods (e.g, TLC, HPLC, GC or NMR) in the art, and a person skilled in the art can determine when to stop the reaction in order to obtain better reaction results according to the testing results (including the conversion degree of the raw materials and the formation of impurities, etc.).

The method for preparing the compound of formula 2 can further comprise carrying out a condensation reaction of a compound of formula A and a compound of formula B in a solvent in the presence of a condensing agent and a base to obtain the compound of formula C;

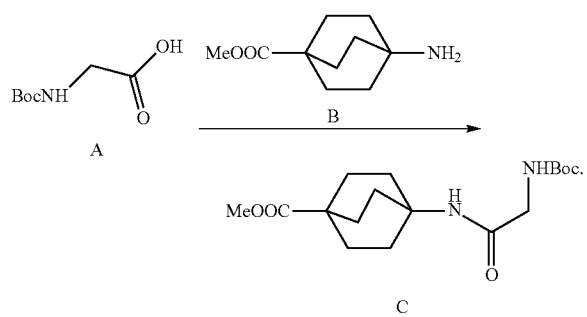

The conditions of the condensation reaction can be conventional conditions of this type of reaction in the art.

In the condensation reaction, the solvent can be one or more selected from the group consisting of a halogenated alkane solvent (e.g., a chloroalkane solvent, e.g., one or more selected from the group consisting of dichloromethane, chloroform, and 1,2-dichloroethane), an amide solvent (e.g., N,N-dimethylformamide) and a nitrile solvent (e.g., acetonitrile).

In the condensation reaction, the condensing agent can be a carbodiimide-based condensing agent, an onium salt-based condensing agent, an organic phosphorus-based condensing agent, or CDI (N,N'-carbonyldiimidazole).

The carbodiimide-based condensing agent can be one or more selected from the group consisting of DCC (dicyclohexylcarbodiimide), EDCI (1-(3-dimethylaminopropyl)-3-ethylcarbodiimide) and DIC (diisopropylcarbodiimide).

The carbodiimide-based condensing agent can be used in combination with an active intermediate stabilizer, which can be one or more selected from the group consisting of DMAP (4-dimethylaminopyridine), HOBt (1-hydroxybenzotriazole), HOAt (1-hydroxy-7-azobenzotriazole), HOSU (N-hydroxysuccinimide), and NHPI (N-hydroxyphthalimide). The molar ratio of the active intermediate stabilizer to the carbodiimide-based condensing agent can be 1:1 to 2:1.

The onium salt-based condensing agent can be one or more selected from the group consisting of HATU (2-(7-azobenzotriazole-1-yl)-N,N,N',N'-tetramethyluronium hexafluorophosphate), HBTU (O-benzotriazol-N,N,N',N'-tetramethyluronium hexafluorophosphate), HCTU (O-(6-chloro-1H-benzotriazol-1-yl)-1,1,3,3-tetramethyluronium hexafluorophosphate) and TBTU (O-benzotriazole-N,N,N',N'-tetramethyluronium tetrafluoroborate).

The organic phosphorus-based condensing agent can be DPP-Cl (diphenylphosphinic chloride) and/or DPPA (diphenylphosphoryl azide).

In some embodiments, the condensing agent is a carbodiimide-based condensing agent. In some embodiments, the condensing agent is EDCI. In some embodiments, the condensing agent is EDCI, which is used in combination with an active intermediate stabilizer. In some embodiments, the condensing agent is EDCI, which is used in combination with HOBt.

In the condensation reaction, the molar ratio of the condensing agent to the compound of formula B can be 1:1 to 5:1, e.g., 1:1 to 2:1.

In the condensation reaction, the base can be one or more selected from the group consisting of

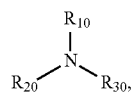

wherein each of $R_{10}$, $R_{20}$, and $R_{30}$ is independently a $C_1$-$C_4$ alkyl. In some embodiments, the base is triethylamine or diisopropylethylamine.

In the condensation reaction, the molar ratio of the base to the compound of formula B can be 1:1 to 10:1, e.g., 5:1 to 6:1.

In the condensation reaction, the molar ratio of the compound of the formula A to the compound of the formula B can be 1:1 to 2:1, e.g, 1.05:1 to 1.2:1.

The progress of the condensation reaction can be monitored by conventional testing methods (e.g, TLC, HPLC, GC or NMR) in the art, and a person skilled in the art can determine when to stop the reaction in order to obtain better reaction results by the testing results (including the conversion degree of raw materials, the formation of impurities, etc.). The reaction time of the condensation reaction can be 10-20 hours.

The present disclosure also provides a method for preparing a compound of formula 4, which comprises the following steps:

(1) preparing a compound of formula 3 according to the method for preparing the compound of formula 3 as described above;

(2) carrying out a Borch reaction of the compound of formula 3 obtained in step (1) and acetaldehyde in a solvent in the presence of an acid and a reducing agent to obtain the compound of formula 4;

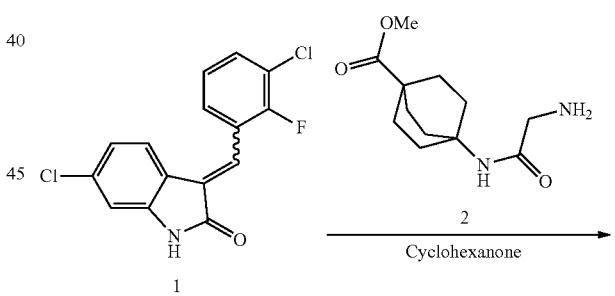

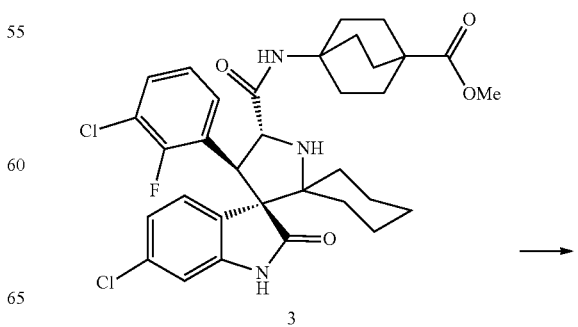

17

-continued

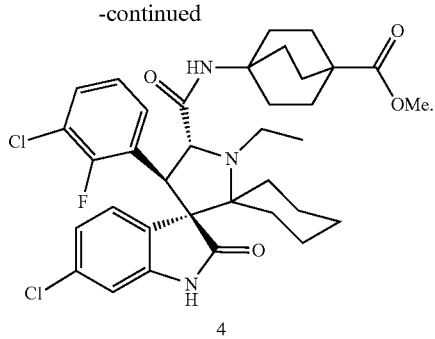

5

The conditions of the Borch reaction can be conventional conditions of this type of reaction in the art.

In the Borch reaction, the solvent can be an organic solvent or a "mixed solvent of an organic solvent and water", wherein the organic solvent can be a chloroalkane solvent (e.g, one or more selected from the group consisting of dichloromethane, chloroform and 1,2-dichloroethane), an aromatic solvent (e.g., toluene and/or xylene), an alcohol solvent (e.g, methanol and/or ethanol), a nitrile solvent (e.g., acetonitrile) and an amide solvent (e.g, N,N-dimethylformamide). When the solvent is a "mixed solvent of an organic solvent and water", the volume ratio of the organic solvent to water can be 1:2 to 10:1. In some embodiments, the solvent is a mixed solvent of dichloromethane and water.

In the Borch reaction, the amount of the solvent can be adjusted according to the reaction scale, the solubility of the reaction raw materials, and the like. For example, the volume/mass ratio of the solvent to the compound of formula 3 can be 5:1 to 50:1 mL/g.

In the Borch reaction, the molar ratio of the acetaldehyde to the compound of formula 3 can be 1:1 to 50:1.

In the Borch reaction, the reagent for providing the acetaldehyde can be 40% acetaldehyde aqueous solution, acetaldehyde or metaldehyde. In some embodiments, the reagent that provides the acetaldehyde is 40% acetaldehyde aqueous solution.

In the Borch reaction, the acid can be acetic acid. The molar ratio of the acid to the compound of formula 3 can be 1:1 to 150:1, e.g., 100:1 to 140:1.

In the Borch reaction, the reducing agent can be a metal borohydride, such as one or more selected from the group consisting of NaCNBH$_3$, NaBH(OAc)$_3$, and NaBH$_4$. In some embodiments, the reducing agent is NaBH(OAc)$_3$.

In the Borch reaction, the molar ratio of the reducing agent to the compound of formula 3 can be 1:1 to 30:1, such as 10:1 to 20:1.

The reaction temperature of the Borch reaction can be −10 to 50° C., e.g., −10 to 10° C.

The progress of the Borch reaction can be monitored by conventional testing methods (e.g, TLC, HPLC, GC or NMR) in the art, and a person skilled in the art can determine when to stop the reaction in order to obtain better reaction results according to the testing results (including the conversion degree of raw materials, the formation of impurities, etc.). The reaction time of the Borch reaction can be 1-5 hours, such as 1-2 hours.

The present disclosure also provides a method for preparing a compound of formula 5, which comprises the following steps:

(a) preparing a compound of formula 4 according to the method for preparing a compound of formula 4 as described above;

18

(b) carrying out a hydrolysis reaction of the compound of formula 4 obtained in step (1) in a solvent in the presence of a base to obtain the compound of formula 5;

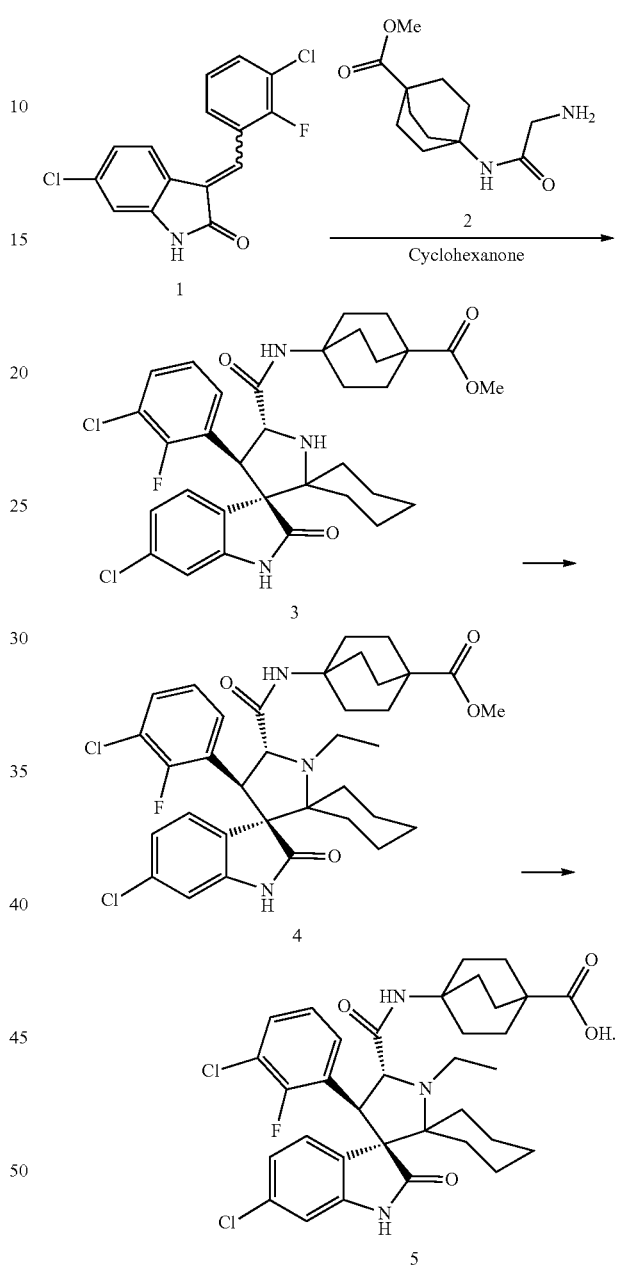

The conditions of the hydrolysis reaction can be conventional conditions of this type of reaction in the art.

In the hydrolysis reaction, the solvent can be a mixed solvent of water, an alcohol solvent (e.g., methanol) and an ether solvent (e.g, tetrahydrofuran), e.g., a mixed solvent of water, methanol and tetrahydrofuran.

In the hydrolysis reaction, the base can be an alkali metal hydroxide, such as one or more selected from the group consisting of sodium hydroxide, potassium hydroxide and lithium hydroxide.

In the hydrolysis reaction, the molar ratio of the base to the compound of formula 4 can be 1:1 to 5:1, e.g., 1:1 to 3:1.

The reaction temperature of the hydrolysis reaction can be 10 to 30° C.

The progress of the hydrolysis reaction can be monitored by conventional testing methods (e.g, TLC, HPLC, GC or NMR) in the art, and a person skilled in the art can determine when to stop the reaction in order to obtain better reaction results according to the testing results (including the conversion degree of the raw materials, the formation of impurities, etc.). The reaction time of the hydrolysis reaction can be 10-20 hours.

The present disclosure also provides a method for preparing a compound of formula 5, wherein the method comprises carrying out a hydrolysis reaction of a compound of formula 4 in a solvent in the presence of a base to obtain the compound of formula 5; the conditions of the hydrolysis reaction can be as described above;

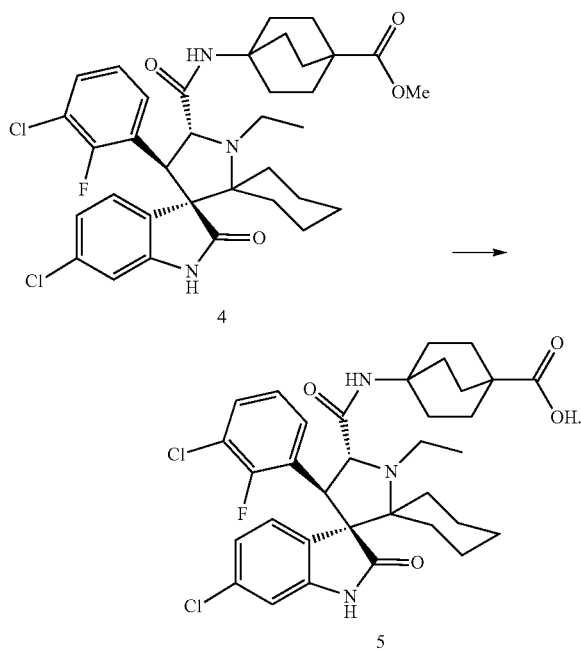

The method for preparing the compound of formula 5 can further comprise a step of preparing the compound of formula 4.

The step of preparing the compound of formula 4 can adopt method A, and the method A can comprise carrying out a Borch reaction of a compound of formula 3 and acetaldehyde in a solvent in the presence of an acid and a reducing agent to obtain the compound of formula 4; the conditions of the Borch reaction can be as described above;

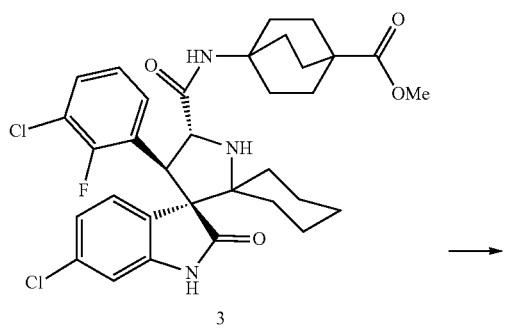

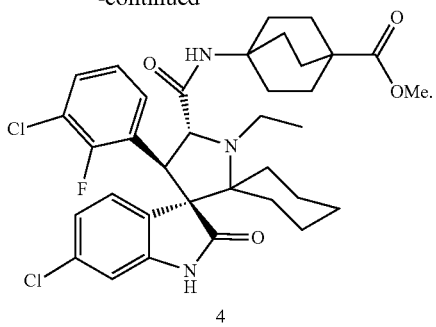

The method A for preparing the compound of formula 4 can further comprise a step of preparing the compound of formula 3, for example, the compound of formula 3 can be prepared according to the method for preparing the compound of formula 3 as described above.

Alternatively, the step of preparing the compound of formula 4 can adopt method B, the method B can comprise carrying out a condensation reaction of a compound of formula 4C and a compound of formula 4B in a solvent in the presence of a condensing agent and a base to obtain the compound of formula 4;

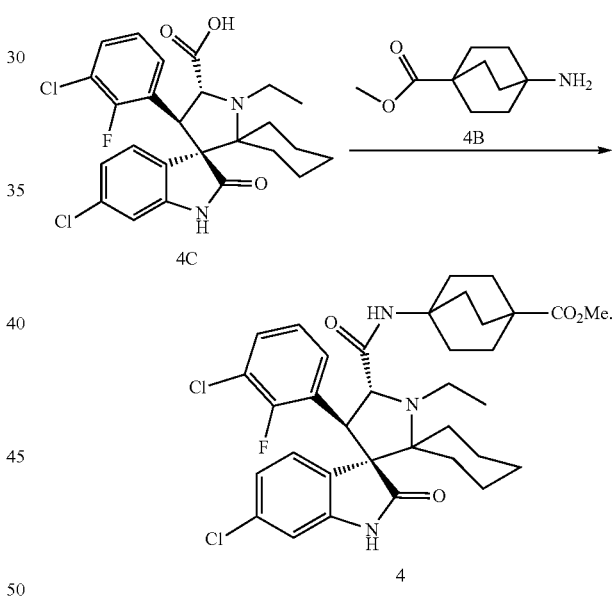

In some embodiments, in the method B for preparing the compound of formula 4, the conditions of the condensation reaction can be conventional conditions of this type of reaction in the art.

In the condensation reaction, the solvent can be one or more selected from the group consisting of a halogenated alkane solvent (e.g., a chloroalkane solvent, e.g., one or more selected from the group consisting of dichloromethane, chloroform and 1,2-dichloroethane), an amide solvent (e.g., N,N-dimethylformamide) and a nitrile solvent (e.g, acetonitrile). In some embodiments, the solvent is dichloromethane.

In the condensation reaction, the condensing agent can be a carbodiimide-based condensing agent or CDI (N,N'-carbonyldiimidazole). In some embodiments, the condensing agent is a carbodiimide-based condensing agent.

The carbodiimide-based condensing agent can be one or more selected from the group consisting of DCC (dicyclohexylcarbodiimide), EDCI (1-(3-dimethylaminopropyl)-3-ethylcarbodiimide) and DIC (diisopropylcarbodiimide).

The carbodiimide-based condensing agent can be used in combination with an active intermediate stabilizer, the active intermediate stabilizer can be one or more selected from the group consisting of DMAP (4-dimethylaminopyridine), HOBt (1-hydroxybenzotriazole), HOAt (1-hydroxy-7-azobenzotriazole), HOSU (N-hydroxysuccinimide), and NHPI (N-hydroxyphthalimide). The molar ratio of the active intermediate stabilizer to the carbodiimide-based condensing agent can be 1:1 to 2:1.

In some embodiments, the condensing agent is EDCI. In some embodiments, the condensing agent is EDCI, which is used in combination with an active intermediate stabilizer. In some embodiments, the condensing agent is EDCI, which is used in combination with HOBt.

In the condensation reaction, the molar ratio of the condensing agent to the compound of formula 4B can be 1:1 to 5:1, e.g, 1:1 to 2:1 (e.g, 1.8:1).

In the condensation reaction, the base can be one or more selected from the group consisting of

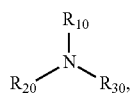

wherein each of $R_{10}$, $R_{20}$ and $R_{30}$ is independently a $C_1$-$C_4$ alkyl. In some embodiments, the base is triethylamine or diisopropylethylamine.

In the condensation reaction, the molar ratio of the base to the compound of formula 4B can be 1:1 to 10:1, e.g., 2:1 to 3:1.

In the condensation reaction, the molar ratio of the compound of the formula 4C to the compound of the formula 4B can be 1:1 to 2:1, e.g, 1.05:1 to 1.2:1 (e.g, 1:1.1).

In some embodiments, in the condensation reaction, the solvent can be dichloromethane; the condensing agent can be EDCI, which is used in combination with HOBt; and the base can be triethylamine.

The progress of the condensation reaction can be monitored by conventional testing methods (e.g, TLC, HPLC, GC or NMR) in the art, and a person skilled in the art can determine when to stop the reaction in order to obtain better reaction results by the testing results (including the conversion degree of raw materials, the formation of impurities, etc.).

The method B for preparing the compound of formula 4 can further comprise a step of preparing the compound of formula 4C. The step for preparing the compound of formula 4C can comprise reacting a compound of formula 3C in a solvent (e.g, ethyl acetate) in the presence of an acid (e.g, HCl) to obtain the compound of formula 4C;

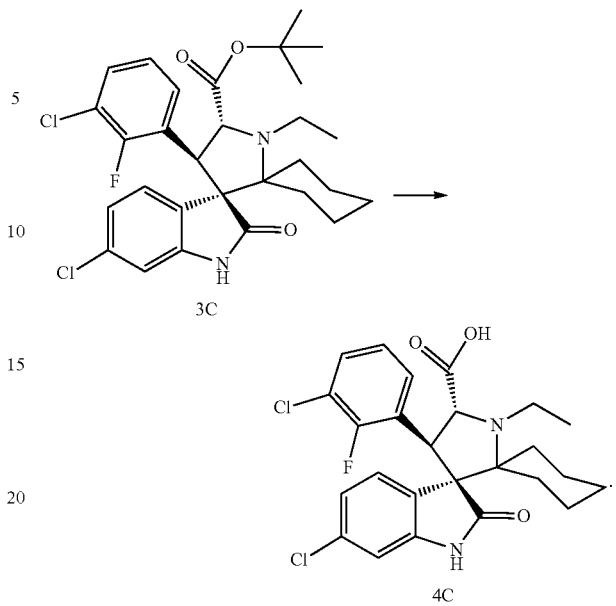

The step of preparing the compound of formula 4C can further comprise a step of preparing the compound of formula 3C, and the step of preparing the compound of formula 3C can comprise carrying out a Borch reaction of a compound of formula 2C and acetaldehyde in the presence of an acid and a reducing agent in a solvent to obtain the compound of formula 3C;

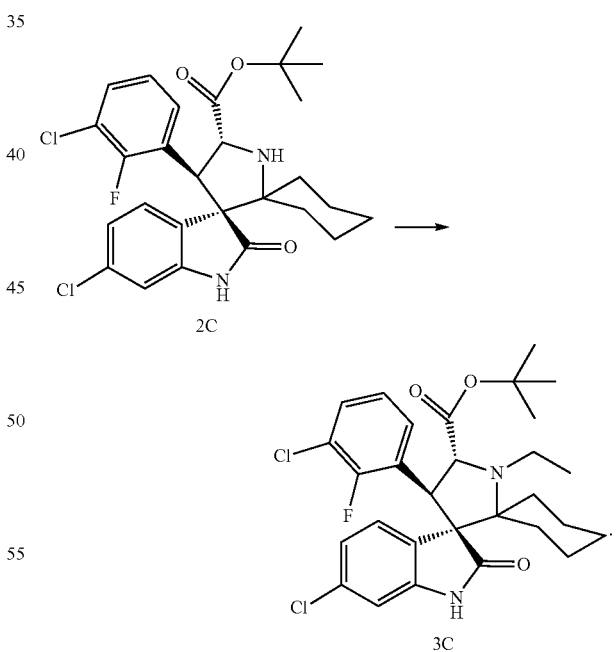

In the step of preparing the compound of formula 3C, in the Borch reaction, the solvent can be an organic solvent or a "mixed solvent of an organic solvent and water", wherein the organic solvent can be one or more selected from the group consisting of a halogenated alkane solvent (e.g, one or more selected from the group consisting of dichloromethane, chloroform and 1,2-dichloroethane), an aromatic solvent (e.g, toluene and/or xylene), an alcohol solvent (e.g, methanol and/or ethanol), a nitrile solvent (e.g, acetonitrile) and an amide solvent (e.g, N,N-dimethylformamide). When the solvent is a "mixed solvent of an organic solvent and water", the volume ratio of the organic solvent to water can be 1:2 to 10:1. In some embodiments, the solvent is a halogenated alkane solvent (e.g, 1,2-dichloroethane). In some embodiments, the solvent is a mixed solvent of a halogenated alkane solvent (e.g, dichloromethane) and water.

In the step of preparing the compound of formula 3C, in the Borch reaction, the amount of the solvent can be adjusted according to the reaction scale, the solubility of the raw materials, and the like. For example, the volume/mass ratio of the solvent to the compound of formula 2C can be 5:1 to 50:1 mL/g, preferably 20:1 to 50:1 mL/g.

In some embodiments, in the step of preparing the compound of formula 3C, in the Borch reaction, the solvent can be a mixed solvent of a chloroalkane solvent (e.g, dichloromethane) and water; wherein the volume/mass ratio of the chloroalkane solvent to the compound of formula 2C can be 5:1 to 40:1 mL/g, preferably 20:1 to 30:1 mL/g; the volume/mass ratio of water to the compound of formula 2C can be 1:1 to 10:1 mL/g.

In the step of preparing the compound of formula 3C, in the Borch reaction, the molar ratio of the acetaldehyde to the compound of formula 2C can be 1:1 to 50:1, e.g., 10:1 to 15:1.

In the step of preparing the compound of formula 3C, in the Borch reaction, the reagent that provides acetaldehyde can be acetaldehyde aqueous solution (e.g, 40% acetaldehyde aqueous solution), acetaldehyde or metaldehyde.

In the step of preparing the compound of formula 3C, in the Borch reaction, the acid can be acetic acid. The molar ratio of the acid to the compound of formula 2C can be 1:1 to 150:1, e.g, 8:1 to 10:1.

In the step of preparing the compound of formula 3C, in the Borch reaction, the reducing agent can be metal borohydride, such as one or more selected from the group consisting of $NaCNBH_3$, $NaBH(OAc)_3$ and $NaBH_4$. In some embodiments, the reducing agent is $NaBH(OAc)_3$.

In the step of preparing the compound of formula 3C, in the Borch reaction, the molar ratio of the reducing agent to the compound of formula 2C can be 1:1 to 30:1, e.g, 5:1 to 10:1 (e.g, 7.2:1).

In the step of preparing the compound of formula 3C, the reaction temperature of the Borch reaction can be −15° C. to 50° C., preferably −15° C. to −5° C. (e.g., −10° C. to −5° C.).

In some embodiments, in the step of preparing the compound of formula 3C, the operation of the Borch reaction can comprise: adding a reducing agent in batches (preferably more than 10 batches) to a mixed solution of the compound of formula 2C, acid, acetaldehyde and a solvent while maintaining the temperature within −15° C. and 5° C. (preferably −15° C. to −5° C., e.g, −10° C. to −5° C.) during the addition of the reducing agent, and then reacting at −10° C. to 50° C. (preferably −15° C. to −5° C., e.g, −10° C. to −5° C.).

The progress of the Borch reaction can be monitored by conventional testing methods (e.g, TLC, HPLC, GC or NMR) in the art, and a person skilled in the art can determine when to stop the reaction in order to obtain better reaction results according to the testing results (including the conversion degree of raw materials, the formation of impurities, etc.). After completion of the reaction, a post treatment step can be performed. The post treatment step can comprise: mixing the reaction solution with ammonium chloride, and then washing and concentrating the obtained organic phase.

The step of preparing the compound of formula 3C can further comprise a step of preparing the compound of formula 2C. The step of preparing the compound of formula 2C can comprise reacting a compound of formula 1 with tert-butyl glycinate and cyclohexanone in an organic solvent in the presence of copper acetate, R-BINAP and a base to obtain the compound of formula 2C;

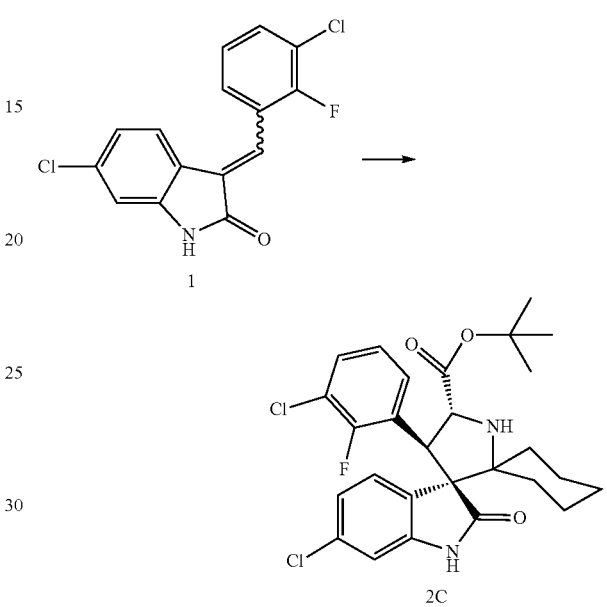

In the step of preparing the compound of formula 2C, the reaction can be performed under a protective gas atmosphere (e.g., one or more selected from the group consisting of nitrogen, helium, neon, argon, krypton, and xenon).

In the step of preparing the compound of formula 2C, the organic solvent can be a conventional solvent used in this type of reaction in the art. In some embodiments, the organic solvent is a cycloalkane solvent (e.g., one or more selected from the group consisting of cyclopentane, cyclohexane and cycloheptane, e.g. cyclohexane) and/or an amide solvent (e.g, N,N-dimethylacetamide and/or N,N-dimethylformamide). In some embodiments, the organic solvent is a cycloalkane solvent (e.g, cyclohexane). In some embodiments, the organic solvent is an amide solvent (e.g, N,N-dimethylacetamide). When the organic solvent is a cycloalkane solvent, the reaction can be promoted by removing the moisture produced during the reaction (e.g, using a water separator or desiccant).

In the step of preparing the compound of formula 2C, the amount of the organic solvent can be adjusted according to the scale of the reaction, the solubility of the raw materials, etc. For example, the volume/mass ratio of the organic solvent to the compound of formula 1 can be 10:1 to 50:1 mL/g.

In the step of preparing the compound of formula 2C, the molar ratio of the tert-butyl glycinate to the compound of formula 1 can be 1:1 to 5:1, e.g, 1:1, 1.5:1, 2:1, 3:1, 4:1 or 5:1.

In the step of preparing the compound of formula 2C, the molar ratio of the cyclohexanone to the compound of formula 1 can be 1:1 to 10:1, e.g, 1:1 to 8:1, e.g, 1:1, 2:1, 3:1, 4:1, 5:1, 6:1, 7:1 or 8:1.

In the step of preparing the compound of formula 2C, the molar ratio of the R-BINAP to the compound of formula 1 can be 0.01:1 to 1:1, e.g., 0.05:1 to 0.5:1, e.g., 0.05:1 to 0.3:1, e.g, 0.05:1, 0.06:1, 0.1:1, 0.13:1, 0.2:1, or 0.3:1.

In the step of preparing the compound of formula 2C, the molar ratio of the copper acetate to the compound of formula 1 can be 0.01:1 to 1:1, e.g, 0.05:1 to 0.5:1, e.g, 0.05:1, 0.1:1, 0.13:1, 0.2:1 or 0.3:1.

In the step of preparing the compound of formula 2C, the base can be an organic base, e.g.,

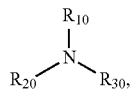

wherein $R_{10}$, $R_{20}$ and $R_{30}$ are independently hydrogen or $C_1$-$C_4$ alkyl. In some embodiments, the base is triethylamine and/or diisopropylethylamine. In some embodiments, the base is triethylamine.

In the step of preparing the compound of formula 2C, the molar ratio of the base to the compound of formula 1 can be 0.01:1 to 5:1, e.g., 0.1:1 to 3:1, e.g., 0.1:1, 0.5:1, 1:1, 2:1 or 3:1.

In the step of preparing the compound of formula 2C, the reaction temperature can be 5° C. to the refluxing temperature of the organic solvent.

In some embodiments, in the step of preparing the compound of formula 2C, the organic solvent can be N,N-dimethylacetamide; the molar ratio of the tert-butyl glycinate to the compound of formula 1 can be 1:1 to 2:1; the molar ratio of the cyclohexanone to the compound of formula 1 can be 1:1 to 2:1; the molar ratio of the R-BINAP to the compound of formula 1 can be 0.05:1 to 0.1:1; the molar ratio of the copper acetate to the compound of formula 1 can be 0.05:1 to 0.1:1; the base can be triethylamine; the molar ratio of the base to the compound of formula 1 can be 0.1:1 to 0.2:1; the reaction temperature can be 5 to 10° C.

In some embodiments, in the step of preparing the compound of formula 2C, the organic solvent can be cyclohexane; the molar ratio of the tert-butyl glycinate to the compound of formula 1 can be 1:1 to 2:1; the molar ratio of the cyclohexanone to the compound of formula 1 can be 6:1 to 8:1; the molar ratio of the R-BINAP to the compound of formula 1 can be 0.1:1 to 0.3:1; the molar ratio of the copper acetate to the compound of formula 1 can be 0.1:1 to 0.3:1; the base can be triethylamine; the molar ratio of the base to the compound of formula 1 can be 1:1 to 3:1; and the reaction temperature can be the refluxing temperature of the organic solvent.

In the step of preparing the compound of formula 2C, the progress of the reaction can be monitored by conventional testing methods (e.g, TLC, HPLC, GC or NMR) in the art, and a person skilled in the art can determine when to stop the reaction in order to obtain better reaction results according to the testing results (including the conversion degree of raw materials, the formation of impurities, etc.).

In the step of preparing the compound of formula 2C, after the reaction is completed, a post-treatment step can be performed. When the reaction solvent is an amide solvent, the post-treatment step can comprise: mixing the reaction mixture with an aqueous solution of ammonium chloride, extracting, concentrating the organic phase, slurrying the residue after concentration with cyclohexane or a mixed solvent of cyclohexane and ethyl acetate, and filtering to obtain a solid. When the reaction solvent is a cycloalkane solvent, the post treatment step can comprise: cooling the reaction mixture to 40 to 45° C., filtering out the solid in the reaction mixture, washing the obtained solid with cyclohexane to give the product.

The present disclosure also provides a compound of any one of the formula as shown below:

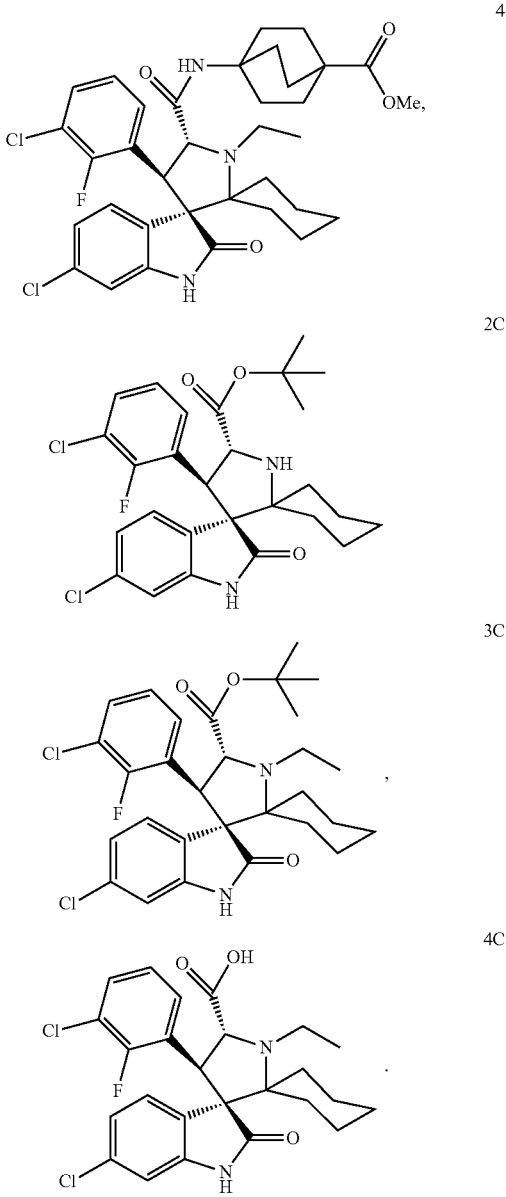

The present disclosure also provides a method for preparing the compound of formula 4, wherein the method is method A or method B; the method A comprises carrying out Borch reaction of a compound of formula 3 and acetaldehyde in a solvent in the presence of an acid and a reducing agent to obtain the compound of formula 4; each step and specific reaction conditions can be as described above;

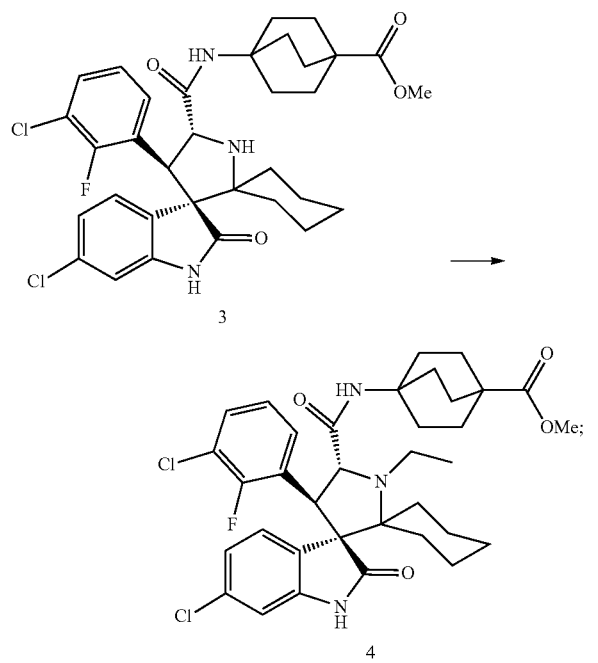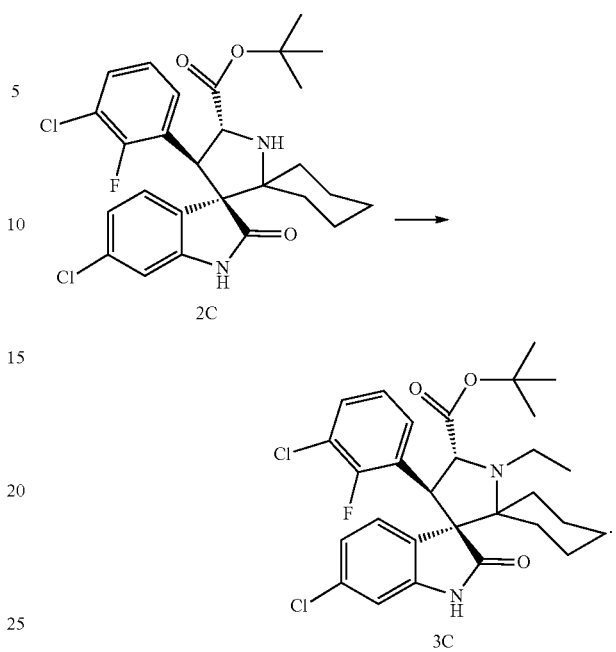

the method B comprises carrying out a condensation reaction of a compound of formula 4C and a compound of formula 4B in a solvent in the presence of a condensing agent and a base to obtain the compound of formula 4; each step and specific reaction conditions can be as described above;

The present disclosure also provides a method for preparing the compound of formula 2C, wherein the method comprises reacting a compound of formula 1 with tert-butyl glycinate and cyclohexanone in an organic solvent in the presence of copper acetate, R-BINAP and a base to obtain the compound of formula 2C; each step and specific reaction conditions can be as described above;

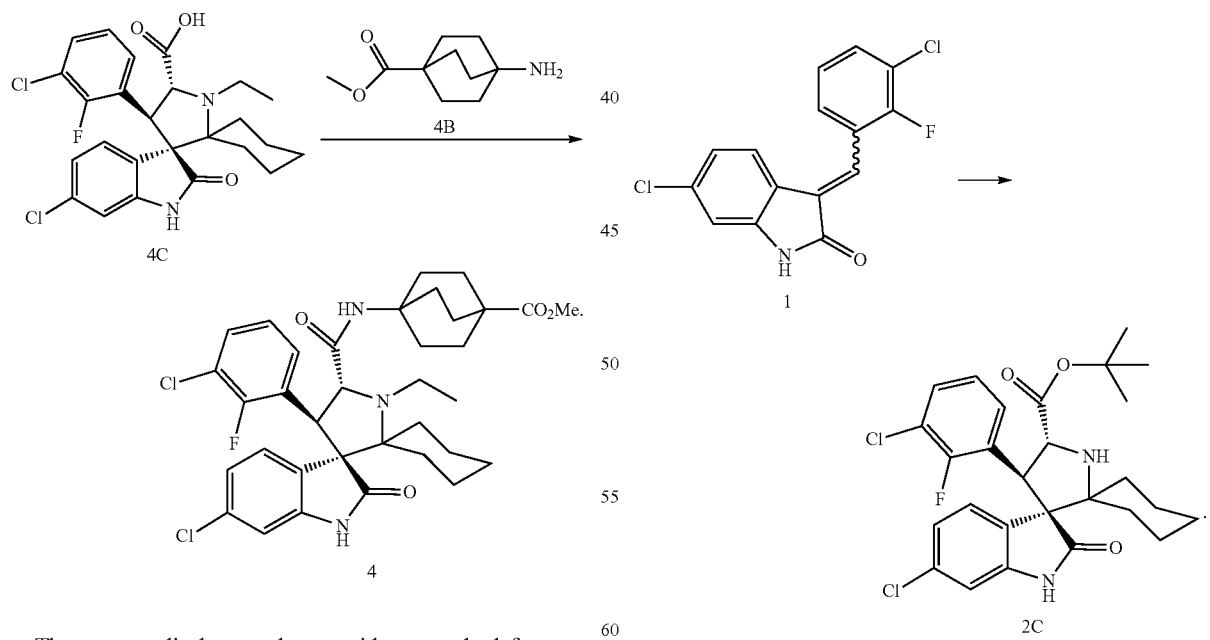

The present disclosure also provides a method for preparing a compound of formula 3C, wherein the method comprises carrying out a Borch reaction of a compound of formula 2C and acetaldehyde in a solvent in the presence of an acid and a reducing agent to obtain the compound of formula 3C; each step and specific reaction conditions can be as described above;

The present disclosure also provides a method for preparing a compound of formula 2, which comprises carrying out a de-Boc reaction on a compound of formula C in a solvent in the presence of an acid to obtain the compound of formula 2;

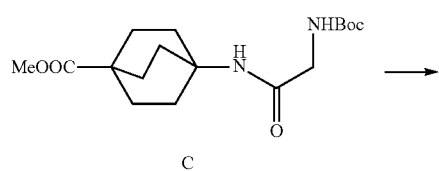

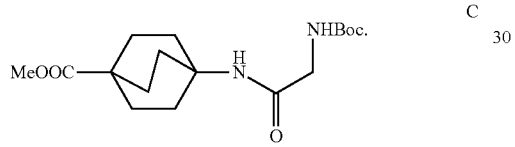

The reaction conditions in each step of the method for preparing the compound of formula 2 can be as described above.

The present disclosure also provides a compound of formula C:

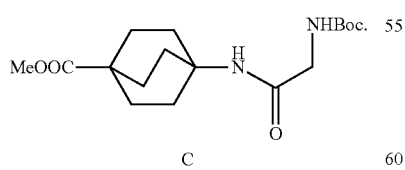

The present disclosure also provides a method for preparing a compound of formula C, which comprises carrying out a condensation reaction of a compound of formula A and a compound of formula B in a solvent in the presence of a condensing agent and a base to obtain the compound of formula C; the conditions of the condensation reaction can be as described above;

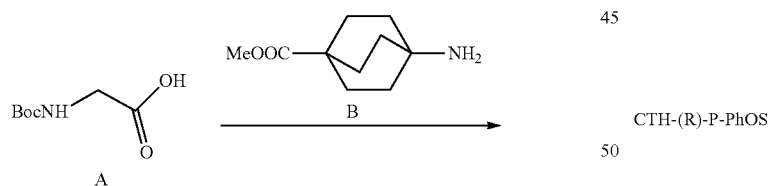

Unless otherwise defined, the compound of formula 1 in the present application refers to an E-configuration compound, a Z-configuration compound, or a mixture thereof.

The following Table 1 shows the structures corresponding to the abbreviations of the phosphine ligands.

TABLE 1

| | |
|---|---|
| (R)-H8-BINAP | 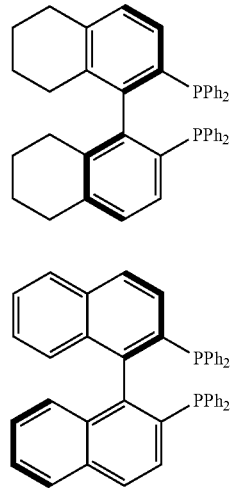 |
| R-BINAP | |
| R-segphos | |
| (R)-C3-TunePhos | |
| CTH-(R)-P-PhOS | 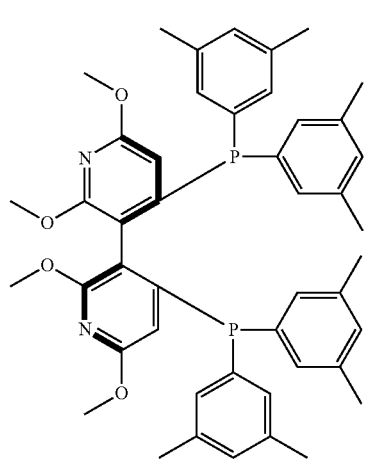 |

TABLE 1-continued (R)-MeO-BIPHEP

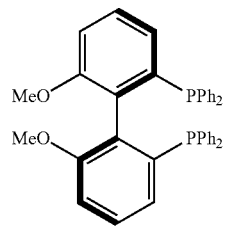

R-3,5-xyl-MeOBIPHE

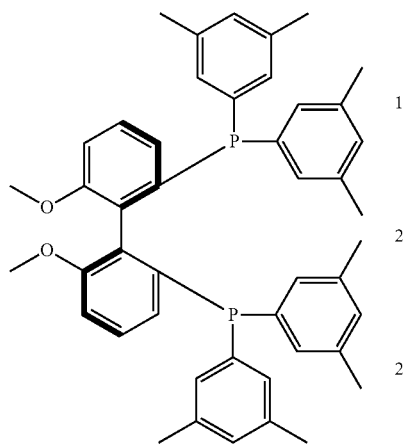

It should be understood by those skilled in the art that, since the present disclosure has disclosed routes for preparing compound 5, i.e., compounds 1+2→3→4→5 and 1→2C→3C→4C→4→5, each reaction step, the preparation method of each intermediate and the routes formed by each reaction step belong to the technical solutions explicitly described in the present disclosure.

Without violating common knowledge in the art, the above-mentioned preferred conditions can be optionally combined to obtain the preferred embodiments of the present disclosure.

The reagents and raw materials used in the present disclosure are all commercially available.

The positive effects of the present disclosure are providing a new method for preparing 2-indolinospirone compound and intermediate thereof which is relatively simple and has high stereoselectivity and yield.

DETAILED DESCRIPTION OF THE EMBODIMENT

The following examples further illustrate the present disclosure, but the present disclosure is not limited thereto.

The experimental methods without indicating specific conditions in the embodiments are performed under conventional methods and conditions, or according to product specifications.

The experimental methods without indicating specific conditions in the following embodiments are performed under conventional methods and conditions. Unless otherwise defined, "room temperature" in the following embodiments means 20° C. to 25° C.

Embodiment 1: 1,3-Dipolar Cycloaddition Reaction

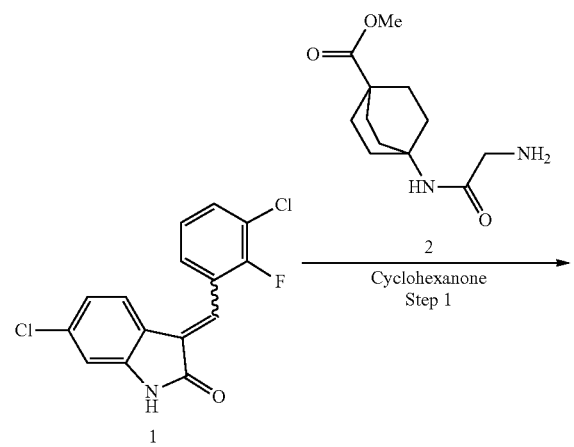

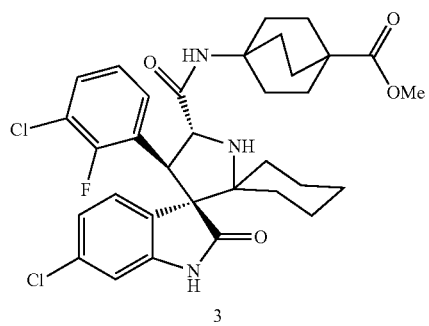

TABLE 2

| | | | | | | | |
|---|---|---|---|---|---|---|---|
| | conditions and results of the 1,3-dipolar cycloaddition reactions | | | | | | |
| Compound of formula 1 | Compound of formula 2 | Metal source | Cyclohexa none | Ligand | Base | Solvent | Result |
| 275 g 0.89 mol | 428.9 g 1.78 mol | CuOAc 14.44 g 0.12 mol | 700.7 g 7.14 mol | R-segphos, 71.93 g 0.12 mol | triethylamine 24.2 g 0.239 mol | cyclohexane 6630 g | yield: 50.2% ee value: 72% |

Cyclohexane, ligand, and metal source were added into a reactor under nitrogen atmosphere, and stirred at 25±5° C. for 2 hours, and then the compound of formula 1 (a mixture of E- and Z-configuration), triethylamine, cyclohexanone, the compound of formula 2 were added sequentially. The reactor was purged with nitrogen, protected by oil seal, and the mixture was heated to reflux for removing water for 30 hours. The progress of the reaction was monitored. The reaction solution in the reactor was cooled until the internal temperature thereof reached 25±5° C., filtered, and the obtained filter cake was dried at 50° C. under vacuum for 3 hours to obtain a crude compound of formula 3.

Ethyl acetate (with a mass of 15 times the mass of the crude compound of formula 3) was added to the crude compound of the formula 3. The resulting mixture was stirred and heated to reflux for 1.5 hours, then stirred for another 2 hours after the internal temperature thereof was cooled to 25±5° C., and filtered by suction filtration. The filter cake was washed with ethyl acetate, dried under vacuum at 48° C. for 14 hours to obtain a first-time refined product of the compound of formula 3.

Ethanol (with a mass of 9 times the mass of the first-time refined product of formula 3) was added to the first-time refined product of the compound of formula 3, and then the obtained mixture was stirred, and heated to reflux. While maintaining the reflux, water was added dropwise, and after the completion of the addition, the stirring was continued under reflux for 2 hours, and then continued for another 2 hours after the internal temperature of the reaction solution was cooled to 25±5° C. The reaction solution was filtered by suction filtration, and the obtained filter cake was dried under vacuum at 65° C. to obtain the compound of formula 3. The total yield was 50.2%, and the ee value was 72%.

TABLE 3

| conditions for determining ee value of the compound of formula 3 | |
|---|---|
| Column | CHIRALCEL IA-3, 150 mm * 4.6 mm, 5.0 μm |
| Mobile phase | n-Hexane:isopropanol:ethanol = 65:10:25 |
| Flow rate | 1.0 mL/minute |
| Column Temperature | 20° C. |
| Injection Volume | 10 μL |
| Isocratic Run Time | 15 minutes |
| UV Detection wavelength | 254 nm |
| Diluent | Isopropanol:ethanol = 1:1 (DCM can be used if the sample did not dissolve) |
| Needle Wash solvent | Diluent |
| Retention time of the compound of formula 3 | 7.317 min |
| Retention time of the isomer | 5.933 min |

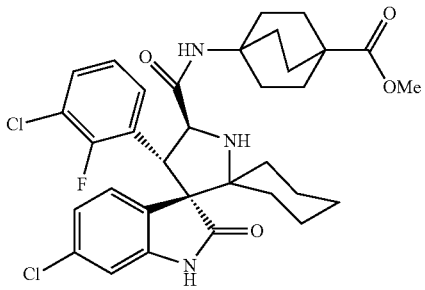

Isomer of the compound of formula 3

The compound of formula 3: $^1$HNMR (400 MHz, DMSO-$d_6$): δ ppm: 10.50 (1H, s), 7.55-7.60 (2H, m), 7.40 (1H, d, J=6.8), 7.32 (1H, t, J=7.2), 7.11 (1H, t, J=8.4), 7.03 (1H, d, J=8.0), 6.65 (1H, s), 4.48 (1H, d, 7=9.2), 4.3 (1H, d, J=8.8), 3.56 (3H, s), 1.92-1.94 (1H, m), 1.79-1.81 (12H, m), 1.32-1.71 (8H, m), 0.78-0.97 (2H, m).

TABLE 4

| other conditions and results of the 1,3-dipolar cycloaddition reaction | | | | | | | |
|---|---|---|---|---|---|---|---|
| Compound of formula 1 | Compound of formula 2 | Metal source | Cyclohexa none | Ligand | Base | Solvent | Result |
| 275 g 0.89 mol | 428.9 g 1.78 mol | CuOAc 14.4 g 0.12 mol | 700.7 g 7.14 mol | (R)-C3-TunePhos 70 g 0.12 mol | triethylamine 24 g 0.24 mol | cyclohexane 6630 g | yield: 62% ee value: 79% |
| 275 g 0.89 mol | 573 g 2.38 mol | CuOAc 14.4 g 0.12 mol | 347.6 g 3.5 mol | R-BINAP 73.15 g 0.12 mol | triethylamine 24 g 0.24 mol | cyclohexane 6630 g | yield: 51% ee value: 65% |
| 275 g 0.89 mol | 573 g 2.38 mol | CuOAc 14.4 g 0.12 mol | 347.6 g 3.5 mol | R-segphos 71.66 g 0.12 mol | triethylamine 24 g 0.24 mol | cyclohexane 6630 g | yield: 77% ee value: 89% |
| 275 g 0.89 mol | 427 g 1.78 mol | CuOAc 14.4 g 0.12 mol | 347.6g 3.5 mol | (R)-H8-BINAP 74 g 0.12 mol | triethylamine 24 g 0.24 mol | cyclohexane 6630 g | yield: 42% ee value: 62% |

TABLE 4-continued other conditions and results of the 1,3-dipolar cycloaddition reaction

| Compound of formula 1 | Compound of formula 2 | Metal source | Cyclohexanone | Ligand | Base | Solvent | Result |
|---|---|---|---|---|---|---|---|
| 275g 0.89 mol | 427g 1.78 mol | CuOAc 14.4 g 0.12 mol | 347.6 g 3.5 mol | (R)-MeO-BIPHEP 68 g 0.12 mol | triethylamine 24g 0.24mol | cyclohexane 6630 g | yield: 56% ee value: 78% |
| 275 g 0.89 mol | 427 g 1.78 mol | CuOAc 14.4 g 0.12 mol | 347.6 g 3.5 mol | (R)-MeO-BIPHEP 68 g 0.12 mol | triethylamine 24 g 0.24 mol | Toluene 7382 g | yield: 61% ee value: 65% |
| 275 g 0.89 mol | 573 g 2.38 mol | CuOAc 14.4 g 0.12 mol | 347.6 g 3.5 mol | R-3,5-xyl-MeOBIPHE 81.6g 0.12 mol | triethylamine 24 g 0.24 mol | cyclohexane 6630 g | yield: 56% ee value: 61% |
| 275 g 0.89 mol | 427 g 1.78 mol | CuOAc 14.4 g 0.12 mol | 700.7 g 7.14 mol | CTH-(R)-P-PhOS 75.65 g 0.12 mol | triethylamine 24 g 0.24 mol | cyclohexane 6630 g | yield: 62% ee value: 68% |
| 275 g 0.89 mol | 427 g 1.78 mol | Cu(OAc)$_2$ 21.4 g 0.12 mol | 347.6 g 3.5 mol | R-segphos 71.66 g 0.12 mol | triethylamine 24 g 0.24 mol | cyclohexane 6630 g | yield: 54% ee value: 89% |
| 275 g 0.89 mol | 427 g 1.78 mol | MgBr$_2$ 21.6 g 0.12 mol | 347.6 g 3.5 mol | R-segphos 71.66 g 0.12 mol | triethylamine 24 g 0.24 mol | cyclohexane 6630 g | yield < 11% |
| 275 g 0.89 mol | 427 g 1.78 mol | FeCl$_2$ 14.9 g 0.12 mol | 347.6 g 3.5 mol | R-segphos 71.66 g 0.12 mol | triethylamine 24 g 0.24 mol | cyclohexane 6630 g | yield: 26% |
| 275 g 0.89 mol | 427 g 1.78 mol | Cu(OTf)$_2$ 42.5g 0.12 mol | 347.6 g 3.5 mol | R-segphos 71.66 g 0.12 mol | triethylamine 24 g 0.24 mol | cyclohexane 6630 g | Yield < 18% |
| 275 g 0.89 mol | 320 g 1.34 mol | CuOAc 5.5 g 0.045 mol | 523.3 g 5.34 mol | R-segphos 32.7 g 0.05 mol | triethylamine 9.1 g 0.09 mol | cyclo-hexane 6630 g | yield: 68% ee value: 56% |
| 275 g 0.89 mol | 320 g 1.34 mol | CuOAc 14.4 g 0.12 mol | 523.3 g 5.34 mol | R-segphos 71.66 g 0.12 mol | triethylamine 9.1 g 0.09 mol | cyclo-hexane 6630 g | yield: 67% ee value: 73% |
| 275 g 0.89 mol | 214 g 0.89 mol | CuOAc 14.4 g 0.12 mol | 700.7 g 7.14 mol | R-segphos 71.66 g 0.12 mol | triethylamine 9.1 g 0.09 mol | cyclo-hexane 6630 g | yield: 34% ee value: 79% |
| 275 g 0.89 mol | 256 g 1.07 mol | CuOAc 14.4 g 0.12 mol | 700.7 g 7.14 mol | R-segphos 71.66 g 0.12 mol | triethylamine 9.1 g 0.09 mol | cyclo-hexane 6630 g | yield: 46% ee value: 75% |

Embodiment 2: Borch Reaction

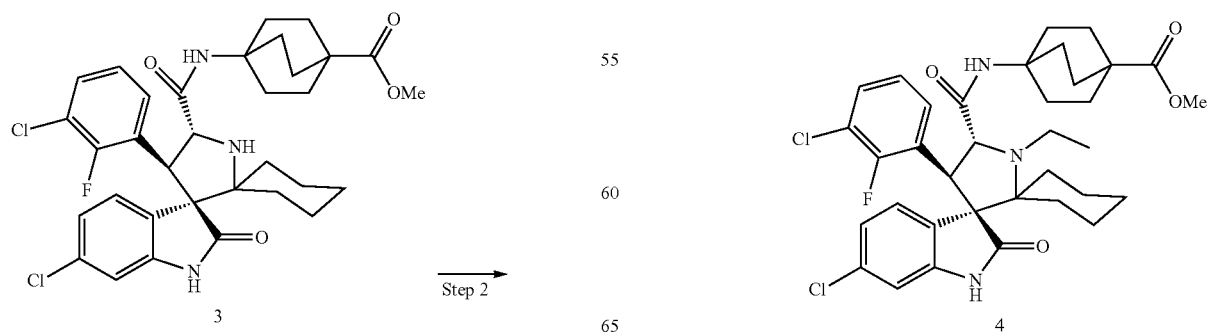

TABLE 5 conditions and results of the Borch reaction

| Compound of formula 3 | NaBH(OAc)$_3$ | 40% acetaldehyde aqueous solution | Acetic acid | Dichloro-methane | Result |
|---|---|---|---|---|---|
| 95 g 0.15 mol | 613 g 2.89 mol | 532.6 g 4.84 mol | 1155 g | 1458 g | Yield: 78% |

Acetic acid, dichloromethane and the compound of formula 3 were added to a reaction flask and stirred. The temperature was lowered to 0 to 5° C. 40% acetaldehyde aqueous solution was added thereto and stirred for 30 minutes. Sodium triacetoxyborohydride was added in portions under an ice bath. After the completion of addition, the ice bath was removed, the temperature was naturally raised to 25±5° C., and the reaction mixture was continued to stir for 1 hour. Saturated ammonium chloride aqueous solution was added to the reaction solution. The obtained mixture was stirred for 20 minutes and separated to obtain an organic phase and an aqueous phase. The organic phase was collected. The aqueous phase was extracted again with dichloromethane. The obtained organic phases were combined, and washed with a sodium bicarbonate aqueous solution until the pH was 8-9. The organic phase was washed with saturated saline, dried, separated by silica gel column chromatography, washed with a mixed solvent (the volume ratio of ethyl acetate to n-heptane is 1:1), and evaporated with a rotary evaporator to remove the solvent to obtain a crude compound of formula 4.

To the above crude compound of formula 4 was added with THF (with a mass of 4 times the mass of the crude compound of formula 4), heated and stirred to reflux till the obtained solution was clear. n-Heptane (with a mass of 10 times the mass of the crude compound of formula 4) was slowly added till a solid precipitated. The obtained mixture was stirred at room temperature 25±5° C. for 3 hours, filtered and dried to obtain the compound of formula 4, yield 78%, ee value 99.69%.

TABLE 6 conditions for measuring ee value of the compound of formula 4

| | |
|---|---|
| Column | CHIRALCEL IA-3, 150 mm * 4.6 mm, 5.0 μm |
| Mobile phase | n-Hexane:isopropanol:ethanol = 65:10:25 |
| Flow rate | 1.0 mL/minute |
| Column Temperature | 20° C. |
| Injection Volume | 10 μL |
| Isocratic Run Time | 15 minutes |
| UV Detection wavelength | 254 nm |
| Diluent | Isopropanol:ethanol = 1:1 (DCM can be used if the sample did not dissolve) |
| Needle Wash solvent | Diluent |
| Retention time of the compound of formula 4 | 10.82 minutes |

The compound of formula 4: $^1$HNMR (400 MHz, DMSO-rife): δ ppm: 10.50 (1H, s), 7.63 (1H, t, J=7.2), 7.30-7.64 (3H, m), 7.11 (1H, t, J=8.0), 7.01 (1H, dd, J$_1$=1.6, J$_2$=8.4), 6.63 (1H, d, J=2.0), 4.30 (1H, d, J=10), 3.92 (1H, d, J=10), 3.57 (3H, s), 3.18-3.33 (2H, m), 2.03-2.05 (1H, m), 1.89-1.92 (1H, m), 1.72-1.79 (12H, m), 1.47-1.68 (6H, m), 1.07 (3H, t, J=6.8), 0.78-0.87 (2H, m).

TABLE 7

Other conditions and results of the Borch reaction

| Compound of formula 3 | NaBH(OAc)$_3$ | Acetaldehyde | Acetic acid | Dichloro-methane | Result |
|---|---|---|---|---|---|
| 95 g 0.15 mol | 613 g 2.89 mol | 40% acetaldehyde aqueous solution 532.6 g 4.84 mol | 1155 g | 1458 g | Yield: 78% |

Embodiment 3: Hydrolysis Reaction

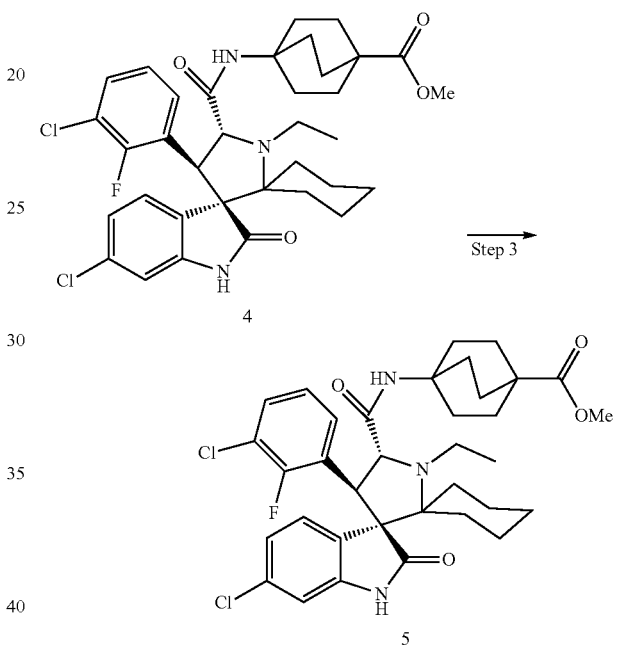

TABLE 8 conditions and results of the hydrolysis reaction

| Compound of formula 4 | LiOH•H$_2$O | NaOH | Solvent system | Result |
|---|---|---|---|---|
| 74.48 g 0.113 mol | 14.28 g 0.34 mol | 13.61 g 0.34 mol | THF 545 mL + CH$_3$OH 545 mL | Yield: 87% |

Sodium hydroxide was dissolved in 272 mL of water, and cooled to below 25° C. for use. Lithium hydroxide monohydrate was dissolved in 273 mL of water, and cooled to below 25° C. for use.

The compound of formula 4, tetrahydrofuran and methanol were added into a reaction flask in one portion and stirred until clear. Sodium hydroxide aqueous solution and lithium hydroxide aqueous solution were respectively added to the reaction flask dropwise. The obtained solution was cooled to below 25° C., and reacted under stirring for 16 hours. After the completion of the reaction, the reaction solution was cooled to 10-20° C. and the pH was adjusted to 6-7 with 6N hydrochloric acid, and then the mixture was stirred for 15 minutes. The mixture was cooled to 10-20° C., added with 595 mL of pure water dropwise. After stirring for 1 hour, the mixture was filtered. The obtained filter cake was washed with pure water, dried to obtain the compound of formula 5, yield 87.4%.

The compound of formula 5: ¹HNMR (400 MHz, DMSO-$d_6$): δ ppm: 12.10 (1H, s), 10.52 (1H, s), 7.64 (1H, t, J=6.8), 7.39 (dd, J=8.4, J=2.4, 1H), 7.36 (s, 1H), 7.11 (1H, t, J=7.6), 7.01 (1H, dd, $J_1$=1.6, $J_2$=8.4), 6.63 (1H, d, J=2.0), 4.29 (1H, d, J=10), 3.92 (1H, d, J=10), 3.33-3.17 (m, 2H), 2.06-2.03 (1H, m), 1.9-1.89 (1H, m), 1.82-1.76 (m, 12H); 1.68-1.59 (2H, m), 1.57-1.44 (m, 3H), 0.87-0.76 (1H, m); 1.61-1.59 (1H, m); 1.08-1.05 (3H, m), 0.99-0.96 (1H, m).

Embodiment 4: Condensation Reaction

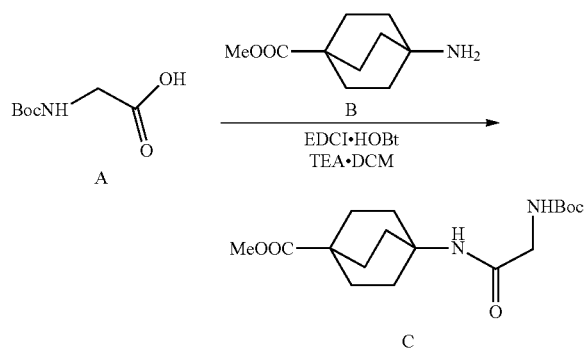

TABLE 9 conditions and results of the condensation reaction

| Compound of formula A | Compound of formula B | Condensation system | Base | Solvent | Result |
|---|---|---|---|---|---|
| 656.8 g 3.75 mol | 652.3 g 3.56 mol | 1440 g EDCI·HCl 1020 g HOBT | Triethylamine 1890 g 18.73 mol | Dichloromethane 14690 g | Yield: 94% |

Dichloromethane, Boc-glycine, triethylamine, HOBt, EDCI hydrochloride, and a compound of formula B were added sequentially under nitrogen atmosphere. After the completion of the addition, the obtained reaction solution was stirred at 25±5° C. for 16 hours, then added with 2N hydrochloric acid aqueous solution, stirred for 30 minutes, and filtered. The obtained filter cake was washed with dichloromethane, and separated to obtain an organic phase.

The organic phase was sequentially washed with dilute hydrochloric acid aqueous solution, alkaline aqueous solution and water, then dried, filtered with silica gel, eluted with a mixed solvent (the volume ratio of dichloromethane to methanol is 50:1), the obtained filtrate was concentrated under reduced pressure to obtain 1195 g of a compound of formula C, yield 94%.

The compound of formula C: ¹HNMR (400 MHz, DMSO-$d_6$): δ ppm 7.23 (1H, s), 6.75 (1H, t, J=5.6), 3.56 (3H, s), 3.42 (2H, d, J=5.6), 1.78-1.79 (12H, m), 1.37 (9H, s).

Embodiment 5: de-Boc Reaction

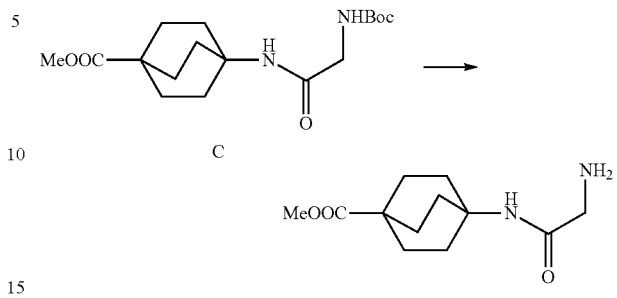

TABLE 10 conditions and results of the de-Boc reaction

| Compound of formula C | Acid | Solvent | Reaction time | Reaction temperature | Result |
|---|---|---|---|---|---|
| 1195 g 3.51 mol | 2.4 L 32% hydrogen chloride ethanol solution | 9.6 L THF | 16 hours | Normal temperature | Yield 90% |

To the above compound of formula C was added tetrahydrofuran and a solution of PGP-IOI TI 32% hydrogen chloride in ethanol, and the mixture was stirred at 25±5° C. for 16 hours. After the completion of the reaction, the resultant reaction solution was filtered, and rinsed with tetrahydrofuran. The obtained filtrates were combined, concentrated, and filtered. To the obtained filter cake was added dichloromethane (with a mass of 10 times the mass of the compound of formula C), and then the pH was adjusted to 8-9 with 8% potassium carbonate aqueous solution. The aqueous phase was washed with dichloromethane for two times. The organic phases were combined, concentrated, added with n-heptane (with a mass of 6 times the mass of the compound of formula C), during which a solid precipitated. The mixture was filtered to obtain the solid, which was dried to obtain the compound of formula 2, yield 90%.

The compound of formula 2: ¹HNMR (400 MHz, DMSO-$d_6$): δ ppm 7.35 (1H, s), 3.56 (3H, s), 2.97 (2H, s), 1.76-1.83 (12H, m).

Embodiment 6

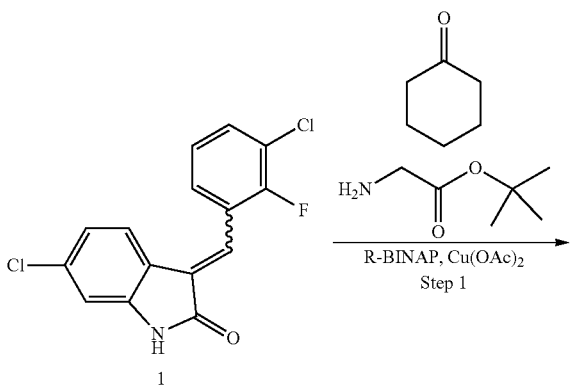

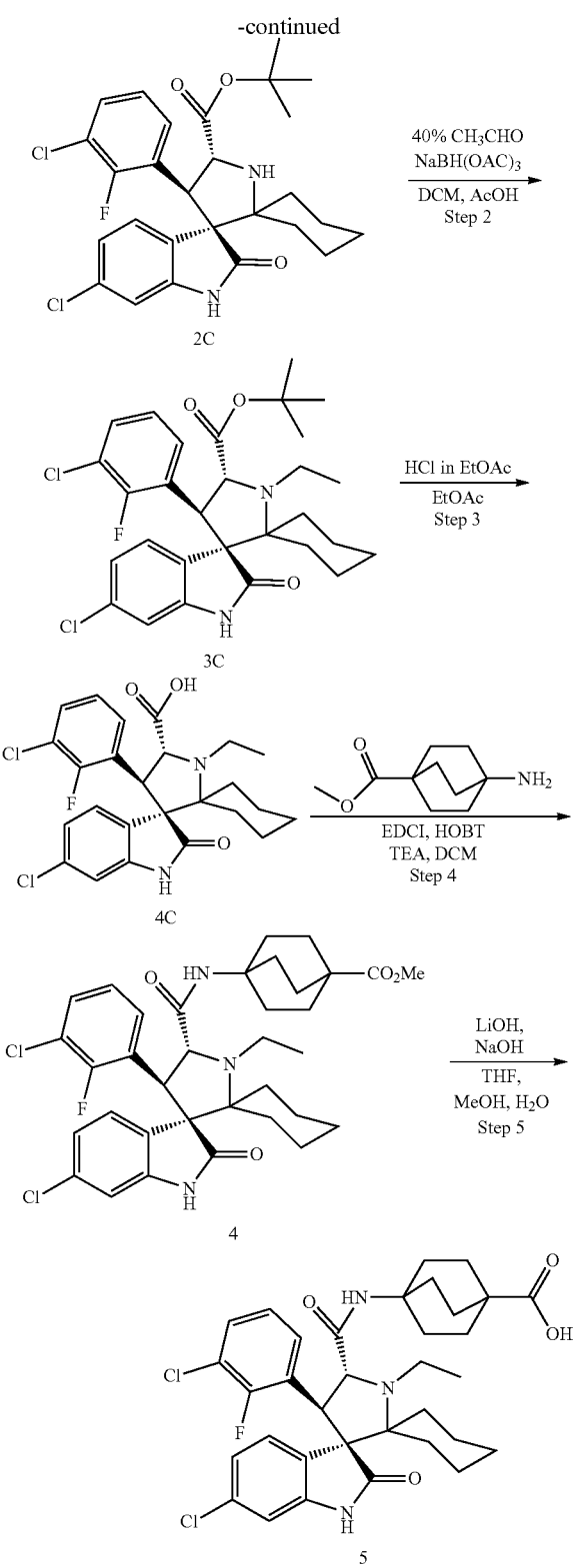

stirred at 5-10° C. After completion of the reaction, the reaction mixture was diluted with ethyl acetate, saturated aqueous solution of ammonium chloride was added, and the precipitated solid was filtered off. The filtrate was allowed to stand to separate into phases. The organic phase was concentrated to give a crude product, which was slurried with a mixed solvent of ethyl acetate/cyclohexane. The mixture was filtered, and the obtained solid was dried to give 17.6 g of the compound of formula 2C with a yield of 52% and ee % of 95%.

Method 2: compound of formula 1 (2.0 g) was added to cyclohexane (100 mL), and then A-BINAP (0.80 g), copper acetate (0.24 g), cyclohexanone (5.10 g), N,N-diisopropylethylamine (2.52 g), and tert-butyl glycinate (1.70 g) were added sequentially. The reaction system was purged with nitrogen for five times, heated to reflux, equipped with water separator, and stirred under reflux. After completion of the reaction, the reaction mixture was cooled to 40-45° C., and filtered. The filter cake was washed with cyclohexane for three times, the filter cake was collected and dried under vacuum to obtain compound of formula 2C with a yield of 43.2% and ee % of 99.4%.

TABLE 11

| conditions for measuring ee value of the compound of formula 2C | |
|---|---|
| Column | CHIRALCEL IA-3, 150 mm * 4.6 mm, 3.0 μm |
| Mobile phase | n-Hexane:isopropanol = 80:20 |
| Flow rate | 1.0 mL/minute |
| Column Temperature | 35° C. |
| Injection Volume | 10 μL |
| Isocratic Run Time | 15 minutes |
| UV Detection wavelength | 254 nm |
| Diluent | n-hexane:isopropanol = 80:20 |
| Needle wash solvent | Diluent |
| Retention time of the compound of formula 2C | 6.2 min |
| Retention time of the isomer | 5.2 min |

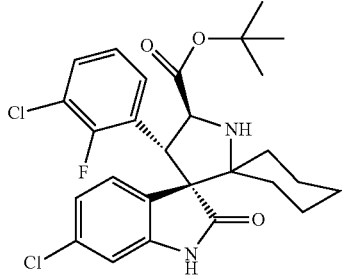

Isomer of the compound of formula 2C

Step 2: Synthesis of Compound of Formula 3C

Compound of formula 2C (15.0 g) obtained in method 1 of step 1 was added to dichloromethane (300 mL), and acetic acid (15 mL) was added. The obtained mixture was cooled to −10 to −5° C. under nitrogen atmosphere, followed by addition of 40% acetaldehyde aqueous solution (38.16 g). The resulting mixture was stirred for 0.5 hour, and then sodium triacetoxyborohydride (44.55 g) was added in batches. After completion of the addition, the reaction mixture was stirred at a temperature controlled at −10 to −5° C. After completion of the reaction, the reaction mixture was diluted with dichloromethane, added with a saturated aqueous solution of ammonium chloride, stirred for 0.5 hour, and Step 1: Synthesis of Compound of Formula 2C Method 1: compound of formula 1 (20 g) was added to N,N-dim ethyl acetamide (400 mL), and then R-BINAP (2.43 g), copper acetate (0.59 g), cyclohexanone (9.75 g), triethylamine (0.99 g) and tert-butyl glycinate (12.77 g) were added sequentially. The reaction system was purged with nitrogen for three times, and the reaction mixture was allowed to stand to separate into phases. The organic phase was washed with saturated sodium bicarbonate solution, water, and saturated aqueous sodium chloride solution sequentially. The organic phase was concentrated to dryness to obtain 17.4 g of a crude product with a yield of 100%, which was used directly in the next step. The compound of formula 3C: $^1$H NMR (400 MHz, DMSO-$d_6$) δ 10.55 (s, 1H), 7.61 (t, J=8.0 Hz, 1H), 7.38 (ddd, J=6.8, 5.2, 1.9 Hz, 2H), 7.15 (t, J=8.0 Hz, 1H), 7.01 (dd, J=8.2, 2.0 Hz, 1H), 6.66 (d, J=2.0 Hz, 1H), 4.50 (d, J=10.2 Hz, 1H), 4.06 (d, J=10.2 Hz, 1H), 3.25 (dq, J=14.6, 7.4 Hz, 1H), 3.13 (dq, J=13.6, 6.8 Hz, 1H), 2.14 (d, J=11.4 Hz, 1H), 1.86 (d, J=13.9 Hz, 1H), 1.70 (q, J=12.5 Hz, 1H), 1.58-1.37 (m, 5H), 1.24 (s, 9H), 1.05 (t, 7=7.1 Hz, 3H), 0.98-0.78 (m, 2H).

Step 3: Synthesis of Compound of Formula 4C

The compound of formula 3C (17.1 g) was added to ethyl acetate (17 mL), a solution of hydrogen chloride in ethyl acetate (170 mL) was added, and the resulting mixture was stirred at room temperature under nitrogen atmosphere. After completion of the reaction, the reaction mixture was concentrated, added with ethyl acetate, and then concentrated to dryness. The crude product was washed with a mixed solvent of ethyl acetate/n-heptane, filtered, and the filter cake was dried to obtain 15.8 g of a compound of formula 4C as a solid, with a yield of 100%.

Step 4: Synthesis of Compound of Formula 5C

Compound of formula 4C (15.7 g) was added to dichloromethane (300 mL), triethylamine (9.70 g), EDCI (12.25 g), HOBt (8.64 g) and methyl 4-aminobicyclo[2.2.2]octane-1-carboxylate (6.44 g) were sequentially added, and the resulting mixture was stirred at room temperature. After completion of the reaction, the reaction mixture was diluted with dichloromethane. The organic phase was washed with dilute hydrochloric acid solution, saturated sodium bicarbonate solution, and saturated sodium chloride solution sequentially, and concentrated to dryness to obtain 20.6 g of the compound of formula 5C with a yield of 98%. The crude product was directly used in the next step.

Step 5: Synthesis of Compound of Formula 5

The compound of formula 5C (20.4 g) was added to a mixed solvent of tetrahydrofuran/methanol (140 mL/140 mL), and a mixed aqueous solution of sodium hydroxide and lithium hydroxide monohydrate (3.73 g/3.91 g dissolved in 140 mL water) was added. The resulting mixture was stirred at room temperature. After completion of the reaction, the pH value of the reaction mixture was adjusted to 4-5 with dilute hydrochloric acid, and seed crystals were added. The mixture was heated to 40° C. and stirred for 1 hour, cooled to 10 to 20° C., added dropwise with water, stirred for 0.5 hour, and filtered to obtain a crude product. The crude product was concentrated to dryness to give 15.4 g with a yield of 77%.

Recrystallization process: the crude product (15.3 g) obtained in the previous step was dissolved in ethyl acetate (500 mL), and the suspended solid particles were filtered off. The filtrate was concentrated under reduced pressure to about 150 mL, and 1.55 g of purified water was added dropwise at room temperature, followed by addition of seed crystals. The resulting mixture was stirred for 1 hour, and 150 mL of n-heptane was added dropwise. The mixture was stirred for 1.5 hours, and then filtered to obtain the product. The product was dried to obtain 11.7 g of the compound of formula 5 with a yield of 76% and ee % of 100%.

TABLE 12

| conditions for measuring ee value of the compound of formula 5 | |
|---|---|
| Column | CHIRALCEL IA-3, 150 mm * 4.6 mm, 3.0 μm |
| Mobile phase | n-Hexane:ethanol:trifluoroacetic acid = 70:30:10 |
| Flow rate | 1.0 mL/minute |
| Column Temperature | 20° C. |
| Injection Volume | 10 μL |
| Isocratic Run Time | 15 minutes |
| UV Detection wavelength | 254 nm |
| Diluent | Isopropanol:ethaol = 1:1 |
| Needle Wash solvent | Diluent |
| Retention time of the compound of formula 5 | 5.1 min |

The compound of formula 5: $^1$H NMR (400 MHz, DMSO-$d_6$) δ 12.08 (s, 1H), 10.50 (s, 1H), 7.63 (ddd, J=8.2, 6.4, 1.6 Hz, 1H), 7.43-7.28 (m, 3H), 7.11 (t, J=8.0 Hz, 1H), 7.01 (dd, J=8.2, 2.0 Hz, 1H), 6.63 (d, J=2.0 Hz, 1H), 4.30 (d, J=10.0 Hz, 1H), 3.92 (d, J=10.0 Hz, 1H), 3.34-3.14 (m, 2H), 2.05 (d, J=11.4 Hz, 1H), 1.91 (d, J=14.1 Hz, 1H), 1.85-1.71 (m, 12H), 1.68-1.43 (m, 6H), 1.07 (t, J=7.1 Hz, 3H), 0.97 (d, J=12.2 Hz, 1H), 0.81 (td, J=13.4, 5.9 Hz, 1H).

It is to be understood that the foregoing description of the embodiments is intended to be purely illustrative of the principles of the disclosure, rather than exhaustive thereof, and that changes and variations will be apparent to those skilled in the art, and that the present disclosure is not intended to be limited other than expressly set forth in the following claims.

What is claimed is:
1. A compound of formula 4:

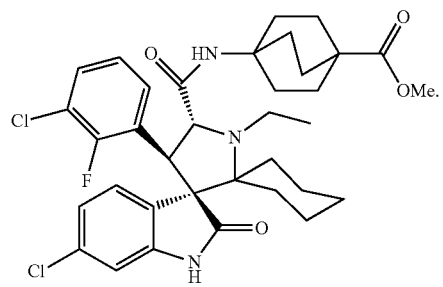

2. A method for preparing the compound of formula 4 of claim 1, comprising step (2): reacting a compound of formula 3:

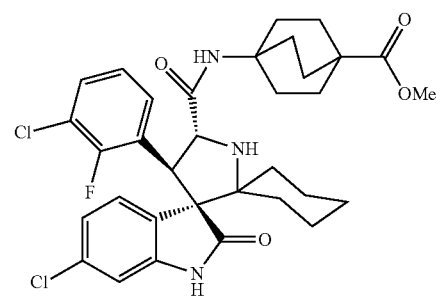

with acetaldehyde in a solvent in the presence of an acid and a reducing agent to obtain the compound of formula 4.

3. A method for preparing a compound of formula 5:

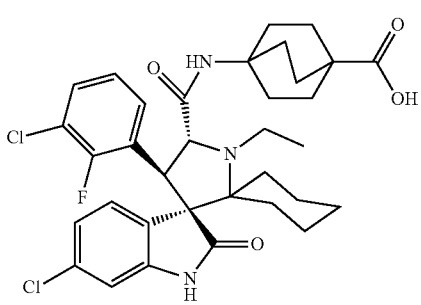

comprising step (2): reacting a compound of formula 3:

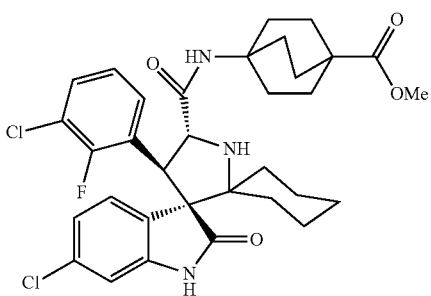

with acetaldehyde in a solvent in the presence of an acid and a reducing agent to obtain a compound of formula 4:

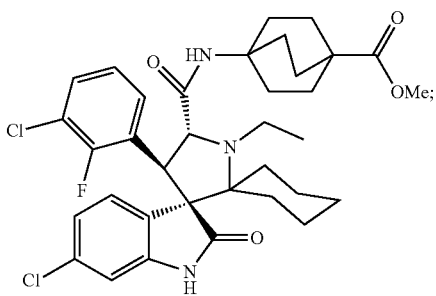

and step (3): hydrolyzing the compound of formula 4 in a solvent in the presence of a base to obtain the compound of formula 5.

4. The method of claim 2, wherein the compound of formula 3 is prepared by a method comprising step (1): reacting a compound of formula 1:

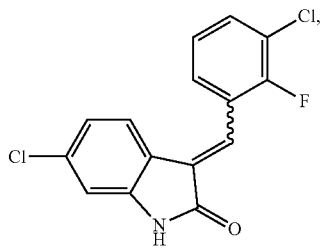

a compound of formula 2:

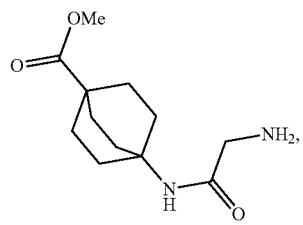

and cyclohexanone in an organic solvent in the presence of a metal source, a phosphine ligand and a base to obtain the compound of formula 3.

5. The method of claim 4, wherein, in step (1), the reaction is carried out under a protective gas atmosphere;

and/or, the organic solvent is one or more selected from the group consisting of an aromatic solvent, an ester solvent, a cycloalkane solvent, an ether solvent, a halogenated alkane solvent, a nitrile solvent, and an amide solvent;

and/or, the volume/mass ratio of the organic solvent to the compound of formula 1 is 10:1 to 50:1 mL/g;

and/or, the molar ratio of the compound of formula 2 to the compound of formula 1 is 1:1 to 5:1;

and/or, the molar ratio of the cyclohexanone to the compound of formula 1 is 1:1 to 10:1;

and/or, the base is an organic base and/or an inorganic base;

and/or, the molar ratio of the base to the compound of formula 1 is 0.01:1 to 2.5:1;

and/or, the reaction temperature of the reaction is 20° C. to the reflux temperature of the organic solvent;

and/or, the metal source is one or more selected from the group consisting of Cu(I) source, Cu(II) source, Ag(I) source, Mg(II) source, Zn(II) source, Ni(II) source and Fe(II) source;

and/or, the molar ratio of the metal source to the compound of formula 1 is 0.01:1 to 1:1;

and/or, the molar ratio of the phosphine ligand to the compound of formula 1 is 0.01:1 to 1:1;

and/or, the phosphine ligand is one or more of a phosphine ligand of formula 6:

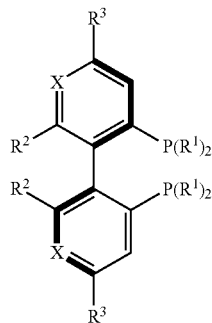

wherein $R^1$ is phenyl, which is optionally substituted by one, two or three substituents independently selected from the group consisting of $C_{1-4}$ alkyl and $C_{1-4}$ alkoxy;

$R^2$ is hydrogen, $C_{1-4}$ alkyl, or $C_{1-4}$ alkoxy groups; alternatively, two $R^2$ are connected to each other and together with the atoms to which they are attached form a 7- to 12-membered carbocyclic ring or 7- to 12-membered heterocyclic ring, the 7- to 12-membered heterocyclic ring contains one, two or three oxygen atoms;

$R^3$ is hydrogen, $C_{1-4}$ alkyl or $C_{1-4}$ alkoxy;

X is N or $CR^4$;

$R^4$ is hydrogen, $C_{1-4}$ alkyl, or $C_{1-4}$ alkoxy; alternatively, $R^4$, its adjacent $R^2$, and together with the atoms to which they are attached form a 5- to 7-membered carbocyclic ring or a 5- to 7-membered heterocyclic ring, the 5- to 7-membered heterocyclic ring contains one, two or three oxygen atoms.

6. The method of claim 5, wherein, in step (1), the protective gas is one or more selected from the group consisting of nitrogen, helium, neon, argon, krypton, and xenon;

and/or, the aromatic solvent is toluene and/or xylene;

and/or, the ester solvent is ethyl acetate and/or isopropyl acetate;

and/or, the cycloalkane solvent is one or more selected from the group consisting of cyclopentane, cyclohexane and cycloheptane;

and/or, the ether solvent is diethyl ether and/or tetrahydrofuran;

and/or, the halogenated alkane solvent is a chloroalkane solvent;

and/or, the nitrile solvent is acetonitrile;

and/or, the amide solvent is N,N-dimethylacetamide and/or N,N-dimethylformamide;

and/or, the volume/mass ratio of the organic solvent to the compound of formula 1 is 20:1 to 40:1 mL/g;

and/or, the molar ratio of the compound of formula 2 to the compound of formula 1 is 1:1 to 3:1;

and/or, the molar ratio of the cyclohexanone to the compound of formula 1 is 1:1 to 8:1;

and/or, the organic base is one or more selected from the group consisting of pyridine, piperidine, DBU, DABCO, and

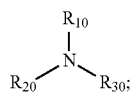

wherein each of $R_{10}$, $R_{20}$ and $R_{30}$ is independently hydrogen or $C_1$-$C_4$ alkyl;

and/or, the inorganic base is one or more selected from the group consisting of an alkali metal alkoxide, an alkali metal carbonate and an alkali metal hydroxide;

and/or, the molar ratio of the base to the compound of formula 1 is 0.1:1 to 2:1;

and/or, the reaction temperature of the reaction is 50° C. to the reflux temperature of the organic solvent;

and/or, the Cu(I) source is one or more selected from the group consisting of CuOAc, CuBr, $Cu_2O$, CuCl, CuI, and $CuPF_6$;

and/or, the Cu(II) source is $Cu(OTf)_2$ and/or $Cu(OAc)_2$;

and/or, the Ag(I) source is one or more selected from the group consisting of AgOAc, AgF, AgBr, and AgOTf;

and/or, the Mg(II) source is $MgCl_2$ and/or $MgBr_2$;

and/or, the Zn(II) source is $Zn(OTf)_2$ and/or $Zn(OAC)_2$;

and/or, the Ni(II) source is $NiCl_2$ and/or $Ni(ClO_4)_2$;

and/or, the Fe(II) source is $FeCl_2$ and/or $FeBr_2$;

and/or, the molar ratio of the metal source to the compound of formula 1 is 0.05:1 to 0.5:1;

and/or, the molar ratio of the phosphine ligand to the compound of formula 1 is 0.05:1 to 0.5:1;

and/or, the phosphine ligand of formula 6 is

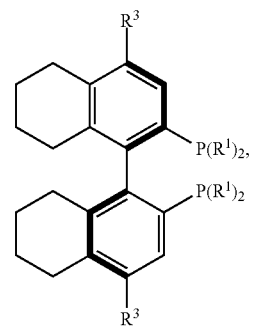

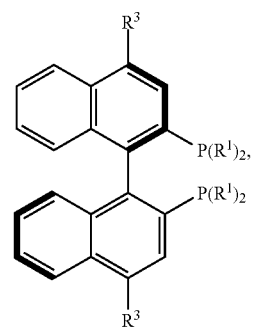

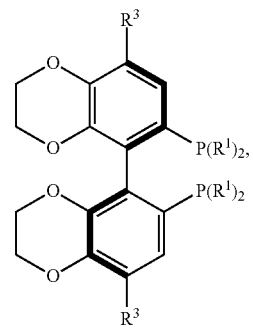

6-4

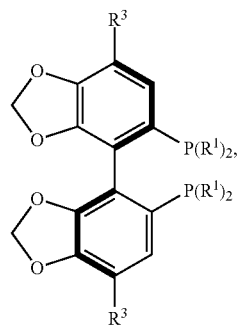

6-5

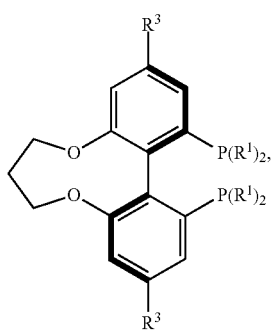

6-6

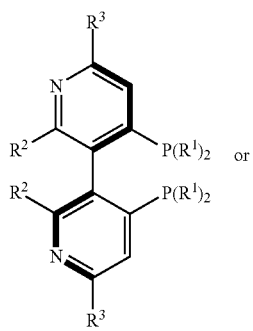

6-7

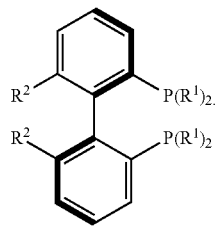

7. The method of claim 6, wherein, in step (1), the aromatic solvent is toluene;
and/or, the cycloalkane solvent is cyclohexane;
and/or, the molar ratio of the compound of formula 2 to the compound of formula 1 is 1.5:1 to 2.7:1;
and/or, the molar ratio of the cyclohexanone to the compound of formula 1 is 1:1, 2:1, 3:1, 4:1, 5:1, 6:1, 7:1 or 8:1;
and/or, the

is triethylamine and/or diisopropylethylamine;
and/or, the alkali metal alkoxide is potassium tert-butoxide and/or sodium tert-butoxide;
and/or, the alkali metal carbonate is potassium carbonate and/or sodium carbonate;
and/or, the alkali metal hydroxide is sodium hydroxide and/or potassium hydroxide;
and/or, the molar ratio of the base to the compound of formula 1 is 0.1:1 to 0.3:1;
and/or, the reaction temperature of the reaction is the reflux temperature of the organic solvent;
and/or, the Cu(I) source is CuOAc;
and/or, the Cu(II) source is $Cu(OAc)_2$;
and/or, the Ag(I) source is AgOAc;
and/or, the Mg(II) source is $MgBr_2$;
and/or, the Fe(II) source is $FeCl_2$;
and/or, the molar ratio of the metal source to the compound of formula 1 is 0.05:1, 0.1:1, 0.13:1, 0.2:1, or 0.3:1;
and/or, the molar ratio of the phosphine ligand to the compound of formula 1 is 0.05:1 to 0.3:1;
and/or, the phosphine ligand of formula 6 is one or more selected from the group consisting of

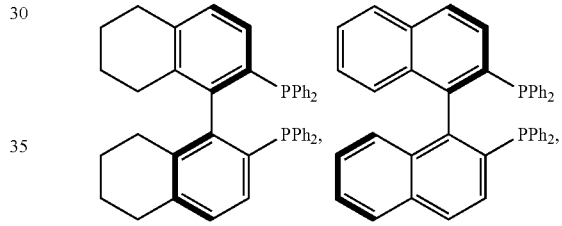

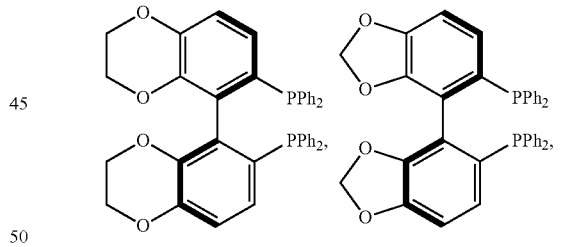

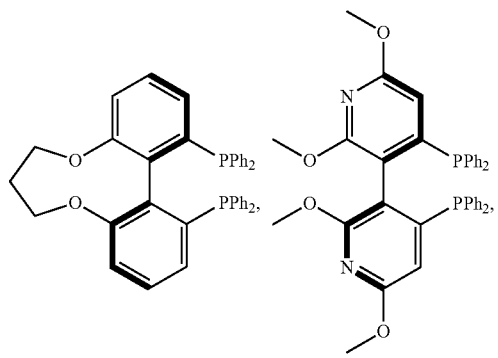

-continued

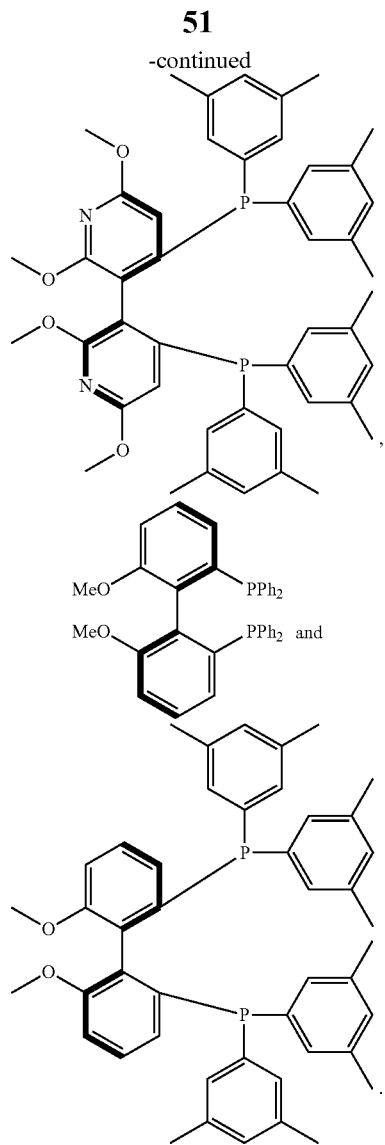

8. The method of claim 5, wherein, in step (1), the organic solvent is a cycloalkane solvent and/or an aromatic solvent; and/or, the base is an organic base;

and/or, the metal source is one or more selected from the group consisting of Cu(I) source, Cu(II) source, Ag(I) source, Mg(II) source and Fe(II) source;

and/or, the phosphine ligand is

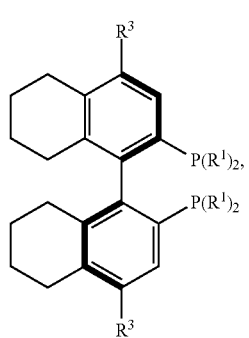

6-1

-continued

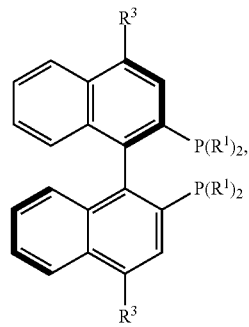

6-2

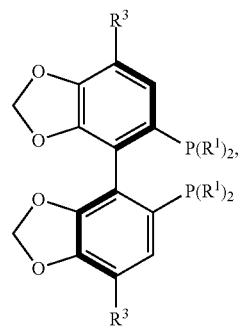

6-4

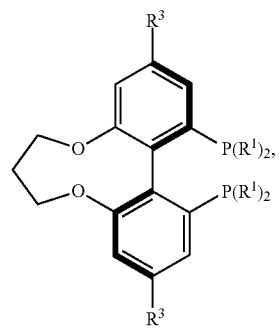

6-5

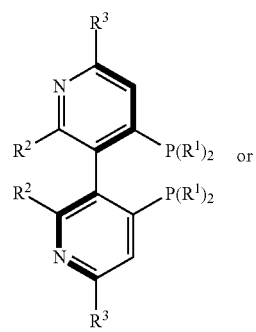

6-6

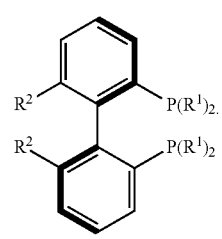

6-7

9. The method of claim 8, wherein, in step (1), the organic solvent is a cycloalkane solvent;

and/or, the base is one or more selected from the group consisting of

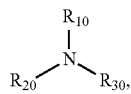

wherein each of $R_{10}$, $R_{20}$ and $R_{30}$ is independently hydrogen or $C_1$-$C_4$ alkyl;

and/or, the metal source is Cu(I) source and/or Cu(II) source;

and/or, the phosphine ligand is 6-2
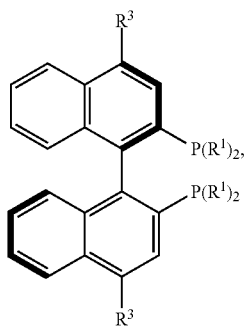

6-4
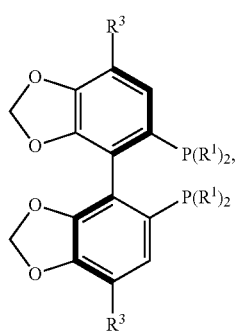

6-5
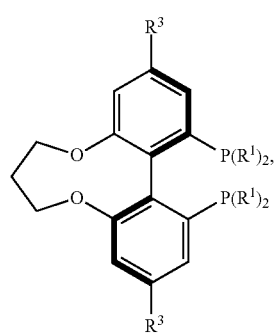

6-6
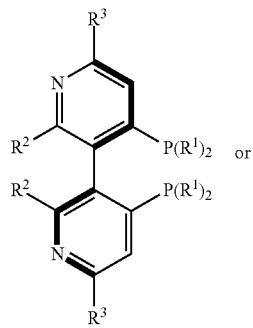

or, 6-7
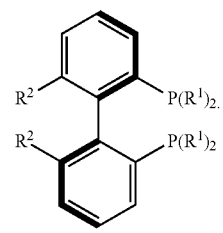

10. The method of claim 9, wherein, in step (1), the organic solvent is cyclohexane;
and/or, the base is triethylamine;
and/or, the metal source is Cu(I) source;
and/or, the phosphine ligand is

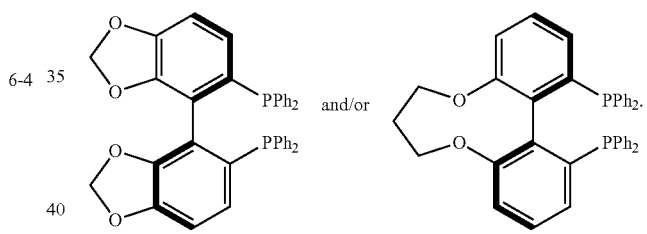

11. The method of claim 4, wherein the compound of formula 2 is prepared by a method comprising reacting a compound of formula C:

C
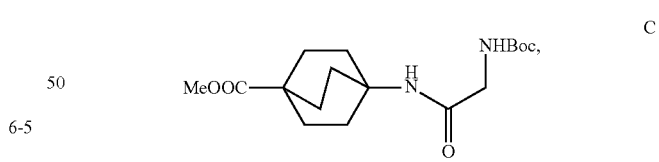

in a solvent in the presence of an acid to obtain the compound of formula 2.

12. The method of claim 2, wherein, in step (2), the solvent is an organic solvent or a mixed solvent of an organic solvent and water;
and/or, the volume/mass ratio of the solvent to the compound of formula 3 is 5:1 to 50:1 mL/g;
and/or, the molar ratio of the acetaldehyde to the compound of formula 3 is 1:1 to 50:1;
and/or, the acetaldehyde is provided from a reagent, which is 40% acetaldehyde aqueous solution, acetaldehyde or metaldehyde;
and/or, the acid is acetic acid;

and/or, the molar ratio of the acid to the compound of formula 3 is 1:1 to 150:1;

and/or, the reducing agent is a metal borohydride;

and/or, the molar ratio of the reducing agent to the compound of formula 3 is 1:1 to 30:1;

and/or, the reaction temperature is −10 to 50° C.

13. The method of claim 12, wherein, in step (2), the organic solvent is a chloroalkane solvent, an aromatic solvent, an alcohol solvent, a nitrile solvent or an amide solvent;

and/or, when the solvent is a mixed solvent of an organic solvent and water, the volume ratio of the organic solvent to water is 1:2 to 10:1;

and/or, the acetaldehyde is provided from a reagent, which is 40% acetaldehyde aqueous solution;

and/or, the molar ratio of the acid to the compound of formula 3 is 100:1 to 140:1;

and/or, the reducing agent is one or more selected from the group consisting of $NaCNBH_3$, $NaBH(OAc)_3$, and $NaBH_4$;

and/or, the molar ratio of the reducing agent to the compound of formula 3 is 10:1 to 20:1;

and/or, the reaction temperature is −10 to 10° C.

14. The method of claim 13, wherein, in step (2), the chloroalkane solvent is one or more selected from the group consisting of dichloromethane, chloroform and 1,2-dichloroethane;

and/or, the aromatic solvent is toluene and/or xylene;

and/or, the alcohol solvent is methanol and/or ethanol;

and/or, the nitrile solvent is acetonitrile;

and/or, the amide solvent is N,N-dimethylformamide;

and/or, the reducing agent is $NaBH(OAc)_3$.

15. The method of claim 3, wherein, in step (3), the solvent is a mixed solvent of water, an alcohol solvent and an ether solvent;

and/or, the base is an alkali metal hydroxide;

and/or, the molar ratio of the base to the compound of formula 4 is 1:1 to 5:1;

and/or, the reaction temperature of the hydrolysis reaction is 10 to 30° C.

16. The method of claim 15, wherein, in step (3), the alcohol solvent is methanol, and the ether solvent is tetrahydrofuran;

and/or, the base is one or more selected from the group consisting of sodium hydroxide, potassium hydroxide and lithium hydroxide;

and/or, the molar ratio of the base to the compound of formula 4 is 1:1 to 3:1.

* * * * *